(12) United States Patent
Tang et al.

(10) Patent No.: US 10,005,729 B2
(45) Date of Patent: Jun. 26, 2018

(54) ORGANIC COMPOUNDS AND ELECTRONIC DEVICE COMPRISING AN ORGANIC LAYER COMPRISING THE ORGANIC COMPOUNDS

(71) Applicants: Dow Global Technologies LLC, Midland, MI (US); Rohm and Haas Electronic Materials Korea Ltd., Cheonan (KR)

(72) Inventors: Zhengming Tang, Shanghai (CN); Chong Xing, Shanghai (CN); Shaoguang Feng, Shanghai (CN); Hong-Yeop Na, Seoul (KR); Minrong Zhu, Shanghai (CN); Robert J. Wright, Sugar Land, TX (US); David D. Devore, Midland, MI (US)

(73) Assignees: ROHM AND HAAS ELECTRONIC MATERIALS KOREA LTD, Cheonan (KR); DOW GLOBAL TECHNOLOGIES LLC, Midland, MI (US)

( * ) Notice: Subject to any disclaimer, the term of this patent is extended or adjusted under 35 U.S.C. 154(b) by 0 days. days.

(21) Appl. No.: 15/537,449

(22) PCT Filed: Dec. 25, 2015

(86) PCT No.: PCT/CN2015/098876
§ 371 (c)(1),
(2) Date: Jun. 19, 2017

(87) PCT Pub. No.: WO2016/101908
PCT Pub. Date: Jun. 30, 2016

(65) Prior Publication Data
US 2018/0002284 A1  Jan. 4, 2018

(51) Int. Cl.
*C07D 209/58* (2006.01)
*H01L 51/50* (2006.01)
*C07D 209/14* (2006.01)
*C09K 11/06* (2006.01)

(52) U.S. Cl.
CPC ......... *C07D 209/58* (2013.01); *C07D 209/14* (2013.01); *C09K 11/06* (2013.01); *H01L 51/5056* (2013.01); *H01L 51/5072* (2013.01); *C09K 2211/1011* (2013.01); *C09K 2211/1029* (2013.01)

(58) Field of Classification Search
CPC .... C07D 209/58; C07D 209/14; C09K 11/06; C09K 2211/1011; C09K 2211/1029; H01L 51/5056; H01L 51/5072
USPC ....................................................... 548/426
See application file for complete search history.

(56) References Cited

U.S. PATENT DOCUMENTS

| | | |
|---|---|---|
| 8,053,457 B2 | 11/2011 | Boettcher et al. |
| 2007/0072002 A1 | 3/2007 | Kim et al. |
| 2008/0269220 A1 | 10/2008 | Yasuma et al. |
| 2011/0240977 A1 | 10/2011 | Jung et al. |
| 2011/0240978 A1 | 10/2011 | Lim et al. |
| 2014/0361259 A1 | 12/2014 | Hwang et al. |

FOREIGN PATENT DOCUMENTS

| | | |
|---|---|---|
| CN | 104725296 A | 6/2015 |
| JP | 2012089777 A | 5/2012 |
| KR | 20150059680 A | 6/2015 |
| KR | 20150121626 A | 10/2015 |
| KR | 20150131700 A | 11/2015 |
| KR | 20150133097 A | 11/2015 |

OTHER PUBLICATIONS

Leo, A. J.; Chemical Reviews, vol. 93, Issue No. 4, p. 1281 (1993).
Polymer Handbook, J. Brandrup and E.H. Immergut, Interscience Pulbishers, 1966.

*Primary Examiner* — Kristin A Vajda
(74) *Attorney, Agent, or Firm* — S. Matthew Cairns

(57) ABSTRACT

Organic compounds suitable for organic layers of electronic devices that show improved luminescent properties.

15 Claims, No Drawings

ORGANIC COMPOUNDS AND ELECTRONIC DEVICE COMPRISING AN ORGANIC LAYER COMPRISING THE ORGANIC COMPOUNDS

FIELD OF THE INVENTION

The present invention relates to organic compounds, and an electronic device comprising an organic layer comprising the organic compounds.

Introduction

Organic light emitting diodes (OLEDs) are used in display devices that employ stacks of films containing organic aromatic compounds as electron transport layers (ETLs) and hole transport layers (HTLs). To compete with other displays such as liquid crystal displays (LCDs), it is important to develop materials with improved properties such as reduced driving voltage and/or increased luminous efficiency to minimize power consumption in OLED displays, especially for mobile applications where batteries are used as power sources. There have been a tremendous amount of research to develop materials to reduce driving voltages and increase luminous efficiency, mostly for hole injection materials (HIMs), such as described in Synthetic Metals, 2009, 159, 69 and J. Phys. D: Appl. Phys. 2007, 40, 5553. There remains a need for new compounds suitable for preparing hole transport layers of OLEDs which have improved properties.

SUMMARY OF THE INVENTION

The present invention provides novel organic compounds, and an electronic device comprising an organic layer comprising the organic compounds.

In a first aspect, the present invention provides organic compounds having the structure represented by Formula (1):

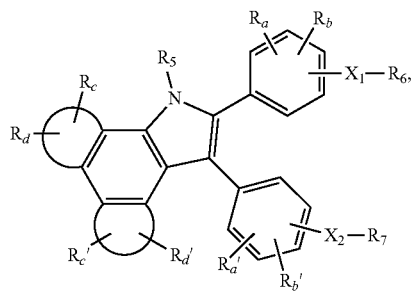

Formula (1)

wherein $R_c$, $R_d$, $R_c'$ and $R_d'$ are each independently selected from the group consisting of hydrogen, deuterium, a substituted or unsubstituted $C_1$-$C_{20}$ alkyl, a substituted or unsubstituted $C_1$-$C_{20}$ alkoxy, a substituted or unsubstituted $C_6$-$C_{20}$ aryl, a substituted or unsubstituted $C_1$-$C_{20}$ heteroaryl, a substituted or unsubstituted $C_6$-$C_{20}$ aryloxy, a halogen, and a cyano;

$R_5$ is selected from the group consisting of hydrogen, deuterium, a substituted or unsubstituted $C_1$-$C_{50}$ alkyl, a substituted or unsubstituted $C_3$-$C_{50}$ cycloalkyl, a substituted or unsubstituted $C_6$-$C_{60}$ aryl, and a substituted or unsubstituted $C_1$-$C_{60}$ heteroaryl;

$R_6$ and $R_7$ are each independently selected from the group consisting of hydrogen, deuterium, a substituted or unsubstituted $C_1$-$C_{50}$ alkyl, a substituted or unsubstituted $C_1$-$C_{50}$ alkoxy, a substituted or unsubstituted $C_1$-$C_{50}$ alkoxycarbonyl, a substituted or unsubstituted $C_6$-$C_{60}$ aryl, a substituted or unsubstituted $C_6$-$C_{60}$ aryloxy, a substituted or unsubstituted $C_6$-$C_{60}$ arylthio, a substituted or unsubstituted $C_1$-$C_{60}$ heteroaryl, a halogen, a cyano, a hydroxyl, a carbonyl, and an amino group substituted with a substituted or unsubstituted $C_6$-$C_{60}$ aryl or a substituted or unsubstituted $C_1$-$C_{60}$ heteroaryl; with the proviso that at least one of $R_6$ and $R_7$ is a substituted amino group having the structure of

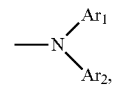

wherein $Ar_1$ and $Ar_2$ are each independently a substituted or unsubstituted $C_6$-$C_{60}$ aryl;

$R_a$, $R_b$, $R_a'$, and $R_b'$ are each independently selected from hydrogen, a substituted or unsubstituted $C_6$-$C_{60}$ aryl or a substituted or unsubstituted $C_1$-$C_{60}$ heteroaryl; and $X_1$ and $X_2$ are each a chemical bond, or each independently selected from the group consisting of a substituted or unsubstituted $C_1$-$C_{50}$ alkylene, a substituted or unsubstituted $C_3$-$C_{50}$ cycloalkylene, a substituted or unsubstituted $C_6$-$C_{60}$ arylene, and a substituted or unsubstituted $C_1$-$C_{60}$ heteroarylene; and optionally $X_1$ and $X_2$ may each independently form one or more rings with the rings they are bonded to.

In a second aspect, the present invention is an electronic device comprising an organic layer, wherein the organic layer comprises the organic compounds of the first aspect.

DETAILED DESCRIPTION OF THE INVENTION

The organic compounds of the present invention may have the structure represented by Formula (1):

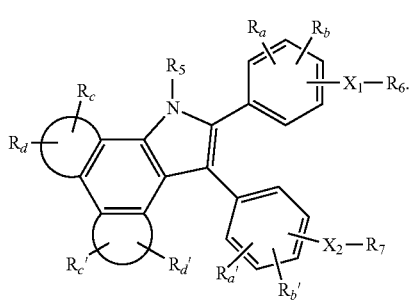

Formula (1)

In Formula (1),

may represent a 5- or 6-membered ring structure and may be each independently selected from the following structure,

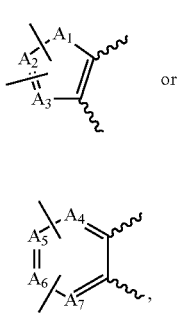

Formula (1R′)

or

Formula (1R″)

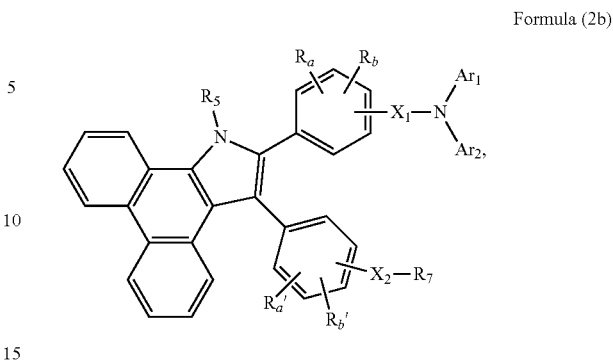

Formula (2b)

wherein $A_1$ is selected from a substituted or unsubstituted heteroatom selected from O, P, S, NR′, PR′, or P(=O)R′; wherein each R′ is hydrogen or a $C_1$-$C_{30}$ hydrocarbyl group;

wherein $A_2$ and $A_3$ are each independently selected from CR′$_2$ or a substituted or unsubstituted heteroatom selected from N, P, PR′$_2$, or P(=O); wherein each R′ is hydrogen or a $C_1$-$C_{30}$ hydrocarbyl group; and wherein $A_4$ through $A_7$ are each independently selected from —CH—, N, P, PR′$_2$, P(=O), or C; wherein each R′ is hydrogen or a $C_1$-$C_{30}$ hydrocarbyl group.

In Formula (1), $X_1$ and $X_2$ may be the same or different. Preferably, $X_1$ and $X_2$ are each a chemical bond. The organic compounds of the present invention comprising a multi-fused indole ring having two substituents at both 2-position and 3-position, which tend to provide devices with higher stability and better performance such as longer life time, increased luminescent efficiency and faster mobility, as compared to those organic compounds comprising a multi-fused indole ring having only one substituent at 2-position or 3-position.

The organic compounds of the present invention may have the structure represented by Formula (2a):

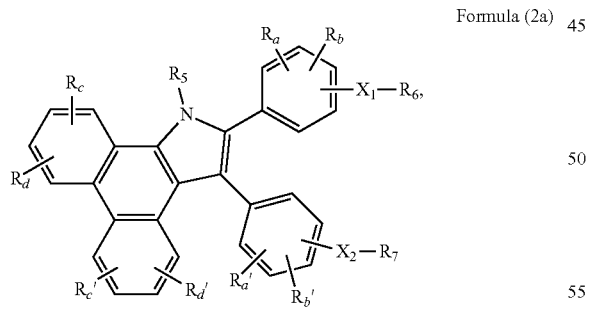

Formula (2a)

wherein $R_c$, $R_d$, $R_c'$, $R_d'$, $R_a$, $R_b$, $R_a'$, $R_b'$, $X_1$, $X_2$, $R_5$, $R_6$ and $R_7$ are as previously defined with reference to Formula (1). Preferably, one of $X_1$ and $X_2$ is arylene and the remaining $X_1$ or $X_2$ is a chemical bond; and $R_c$, $R_d$, $R_c'$, $R_d'$ are each hydrogen. More preferably, $X_1$ and $X_2$ are each a chemical bond; and $R_c$, $R_d$, $R_c'$, $R_d'$ are each hydrogen.

The organic compound of the present invention may have the structure represented by Formula (2b), wherein $R_7$ is selected from the group consisting of hydrogen, deuterium, a substituted or unsubstituted $C_1$-$C_{50}$ alkyl, a substituted or unsubstituted $C_1$-$C_{50}$ alkoxy, a substituted or unsubstituted $C_1$-$C_{50}$ alkoxycarbonyl, a substituted or unsubstituted $C_6$-$C_{60}$ aryl, a substituted or unsubstituted $C_6$-$C_{60}$ aryloxy, a substituted or unsubstituted $C_6$-$C_{60}$ arylthio, a substituted or unsubstituted $C_1$-$C_{60}$ heteroaryl, a halogen, a cyano, a hydroxyl, and a carbonyl; and $R_5$, $R_a$, $R_b$, $R_a'$, $R_b'$, $X_1$, $X_2$, $Ar_1$ and $Ar_2$ are as previously defined with reference to Formula (1). Preferably, one of $X_1$ and $X_2$ is arylene and the remaining $X_1$ or $X_2$ is a chemical bond, and one of $R_a$, $R_b$, $R_a'$, $R_b'$ is aryl. More preferably, $X_1$ and $X_2$ are each a chemical bond; and $R_a$, $R_b$, $R_a'$ and $R_b'$ are each hydrogen.

The organic compounds of the present invention may have the structure represented by Formula (2c):

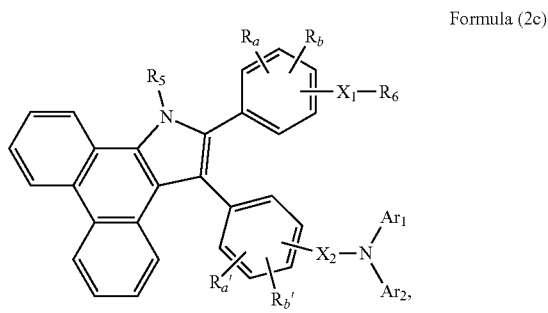

Formula (2c)

wherein $R_6$ is selected from the group consisting of hydrogen, deuterium, a substituted or unsubstituted $C_1$-$C_{50}$ alkyl, a substituted or unsubstituted $C_1$-$C_{50}$ alkoxy, a substituted or unsubstituted $C_1$-$C_{50}$ alkoxycarbonyl, a substituted or unsubstituted $C_6$-$C_{60}$ aryl, a substituted or unsubstituted $C_6$-$C_{60}$ aryloxy, a substituted or unsubstituted $C_6$-$C_{60}$ arylthio, a substituted or unsubstituted $C_1$-$C_{60}$ heteroaryl, a halogen, a cyano, a hydroxyl, and a carbonyl; and $R_5$, $R_a$, $R_b$, $R_a'$, $R_b'$, $X_1$, $X_2$, $Ar_1$ and $Ar_2$ are as previously defined with reference to Formula (1). Preferably, one of $X_1$ and $X_2$ is arylene and the remaining $X_1$ or $X_2$ is a chemical bond, and one of $R_a$, $R_b$, $R_a'$ and $R_b'$ is aryl. More preferably, $X_1$ and $X_2$ are each a chemical bond, and $R_a$, $R_b$, $R_a'$, $R_b'$ are each hydrogen.

The organic compounds of the present invention may have the structure represented by Formula (3a):

Formula (3a)

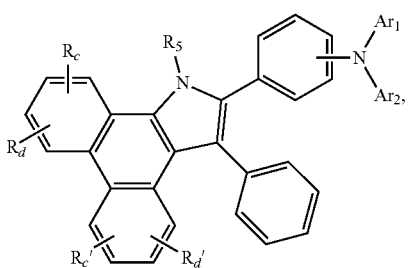

wherein $R_5$, $R_c$, $R_d$, $R_c'$, $R_d'$, $Ar_1$ and $Ar_2$ are as previously defined with reference to Formula (1). Preferably, one of $X_1$ and $X_2$ is arylene and the remaining $X_1$ or $X_2$ is a chemical bond, and $R_c$, $R_d$, $R_c'$, $R_d'$ are each hydrogen. More preferably, $X_1$ and $X_2$ are each a chemical bond, and $R_c$, $R_d$, $R_c'$, $R_d'$ are each hydrogen.

The organic compounds of the present invention may have the structure represented by Formula (3b):

Formula (3b)

wherein $R_5$, $R_c$, $R_d$, $R_c'$, $R_d'$, $Ar_1$ and $Ar_2$ are as previously defined with reference to Formula (1). Preferably, one of $X_1$ and $X_2$ is arylene and the remaining $X_1$ or $X_2$ is a chemical bond, and $R_c$, $R_d$, $R_c'$, $R_d'$ are each hydrogen. More preferably, $X_1$ and $X_2$ are each a chemical bond, and $R_c$, $R_d$, $R_c'$, $R_d'$ are each hydrogen.

In some preferred embodiments, the organic compounds of the present invention have the structure represented by Formula (3c) or (3d):

Formula (3c)

Formula (3d)

wherein $R_5$, $R_c$, $R_d$, $R_c'$, $R_d'$, $Ar_1$ and $Ar_2$ are as previously defined with reference to Formula (1).

$X_1$ and $X_2$ in Formulae (1), (2a), (2b), and (2c) may be the same or different. In some embodiments, $X_1$ and $X_2$ are each independently a chemical bond. "Chemical bond" herein means that two groups bonded to the chemical bond are directly linked to each other. For example, in formula (1), when $X_1$ is a chemical bond, it means that $R_6$ is directly linked to the phenyl group that $X_1$ is bonded to. In some other embodiments, $X_1$ and $X_2$ in Formulae (1), (2a), (2b), and (2c) can be each independently selected from the group consisting of a substituted or unsubstituted $C_1$-$C_{50}$ alkylene, $C_1$-$C_{30}$ alkylene, $C_1$-$C_{20}$ alkylene, or $C_1$-$C_{10}$ alkylene; a substituted or unsubstituted $C_3$-$C_{50}$ cycloalkylene, $C_3$-$C_{30}$ cycloalkylene, $C_4$-$C_{20}$ cycloalkylene, or $C_5$-$C_{10}$ cycloalkylene; a substituted or unsubstituted $C_6$-$C_{60}$ arylene, $C_6$-$C_{30}$ arylene, $C_6$-$C_{20}$ arylene, or $C_6$-$C_{12}$ arylene; and a substituted or unsubstituted $C_1$-$C_{60}$ heteroarylene, $C_1$-$C_{30}$ heteroarylene, $C_4$-$C_{20}$ heteroarylene, or $C_5$-$C_{10}$ heteroarylene. Examples of $X_1$ and $X_2$ include In Formulae (1), (2a), (2b), (2c), (3a), (3b), (3c) and (3d), $R_5$ can be a substituted or unsubstituted $C_1$-$C_{30}$ alkyl, $C_1$-$C_{20}$ alkyl, $C_1$-$C_{10}$ alkyl, $C_1$-$C_5$ alkyl, or $C_1$-$C_3$ alkyl; a substituted or unsubstituted $C_3$-$C_{50}$ cycloalkyl, $C_4$-$C_{30}$ cycloalkyl, $C_4$-$C_{20}$ cycloalkyl, or $C_4$-$C_{12}$ cycloalkyl; a substituted or unsubstituted $C_6$-$C_{60}$ aryl, $C_6$-$C_{30}$ aryl, $C_6$-$C_{20}$ aryl, or $C_6$-$C_{12}$ aryl; or a substituted or unsubstituted $C_1$-$C_{60}$ heteroaryl, $C_1$-$C_{30}$ heteroaryl, $C_2$-$C_{20}$ heteroaryl, or $C_4$-$C_{12}$ heteroaryl. Preferably, $R_5$ is selected from the group consisting of —$CH_3$, —$CH_2CH_3$, $CD_3$,

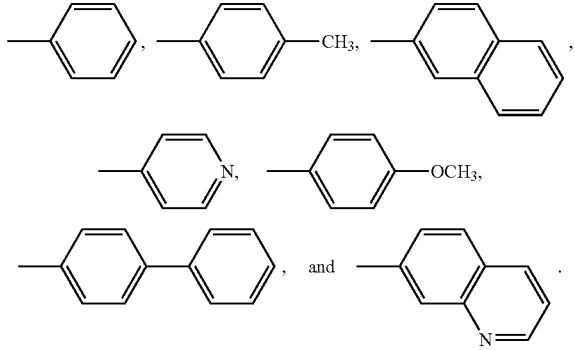

More preferably, $R_5$ is —$CH_3$.

Preferably, the organic compounds of the present invention comprise only one substituted amino group. That is, in Formulae (1), (2a), (2b), and (2c), only one of $R_6$ and $R_7$ is the substituted amino group. Preferably, one of $R_6$ and $R_7$ is the substituted amino group, and the remaining $R_6$ or $R_7$ is selected from hydrogen, a halogen such as F, or a substituted or unsubstituted $C_6$-$C_{60}$ aryl.

The substituted amino group useful in the present invention, e.g., in Formulae (1), (2a), (2b), (2c), (3a) and (3b), may be represented by Formula (A),

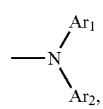

Formula (A)

wherein $Ar_1$ and $Ar_2$ are each independently a substituted or unsubstituted $C_6$-$C_{60}$ aryl. In Formulae (1), (2a), (2b), (2c), (3a), (3b), (3c) and (3d), $Ar_1$ and $Ar_2$ are each independently selected from a substituted or unsubstituted $C_6$-$C_{60}$ aryl, $C_6$-$C_{30}$ aryl, $C_{12}$-$C_{30}$ aryl, $C_6$-$C_{20}$ aryl, $C_{12}$-$C_{20}$ aryl, or $C_6$-$C_{15}$ aryl. Preferably, $Ar_1$ and $Ar_2$ are each independently a substituted or unsubstituted $C_{12}$-$C_{30}$ aryl, and most preferably, a substituted or unsubstituted $C_{12}$-$C_{20}$ aryl.

The substituted amino group useful in the present invention may be each independently selected from the following structures represented by Formula (4a) through Formula (4c):

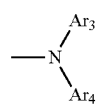

Formula (4a)

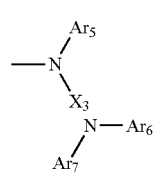

Formula (4b)

Formula (4c)

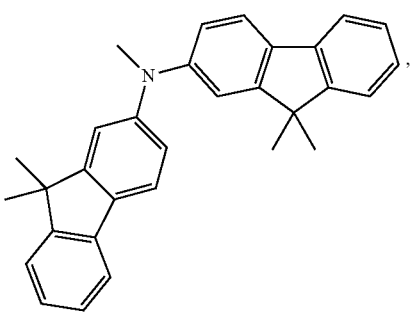

wherein $Ar_3$ and $Ar_4$ are each independently a unsubstituted $C_6$-$C_{60}$ aryl, $Ar_5$ through $Ar_7$ are each independently a unsubstituted $C_6$-$C_{40}$ aryl, and $Ar_8$ through $Ar_{11}$ are each independently a unsubstituted $C_6$-$C_{30}$ aryl; and $X_3$ through $X_5$ are each independently selected from the group consisting of a substituted or unsubstituted $C_6$-$C_{60}$ arylene and a substituted or unsubstituted $C_1$-$C_{60}$ heteroarylene. Preferably, at least one of $R_6$ and $R_7$ has the structure of Formula (4a). $X_3$ through $X_5$ may be each independently selected from a substituted or unsubstituted $C_6$-$C_{60}$ arylene, $C_6$-$C_{30}$ arylene, $C_6$-$C_{20}$ arylene, or $C_6$-$C_{12}$ arylene, and a substituted or unsubstituted $C_1$-$C_{60}$ heteroarylene, $C_1$-$C_{30}$ heteroarylene, $C_2$-$C_{20}$ heteroarylene, or $C_4$-$C_{12}$ heteroarylene. Preferably, $Ar_3$ through $Ar_{11}$ may be each a unsubstituted $C_6$-$C_{30}$ aryl, $C_6$-$C_{20}$ aryl, $C_6$-$C_{15}$ aryl, or $C_6$-$C_{12}$ aryl.

Examples of suitable substituted amino groups useful in the present invention include the following structures (5-1) through (5-6):

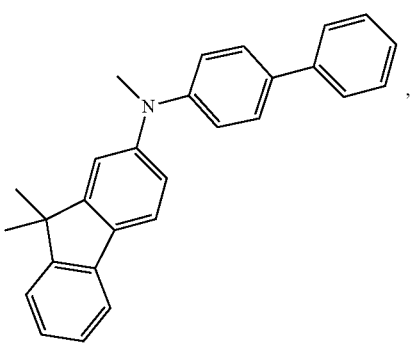

(5-1)

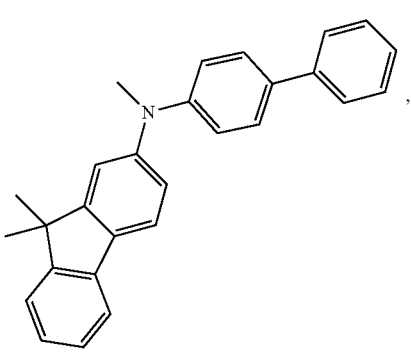

(5-2)

-continued

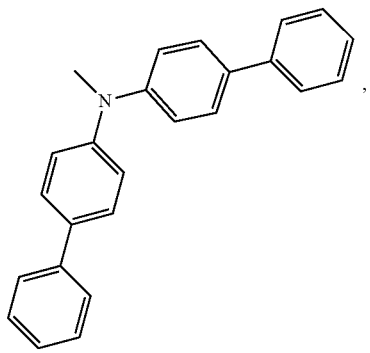
(5-3)

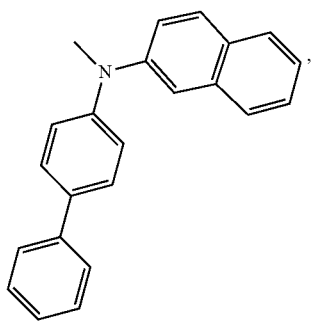
(5-4)

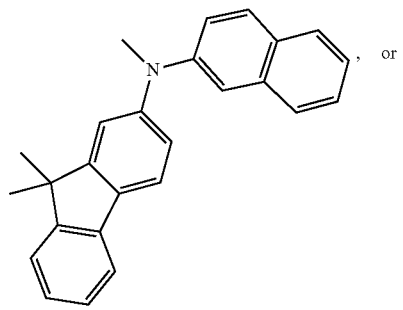
(5-5)

, or

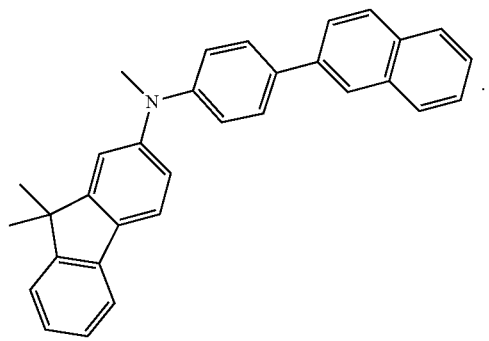
(5-6)

In Formulae (1), (2a), (2b) and (2c), respectively, $R_a$, $R_b$, $R_a'$ and $R_b'$ are each independently selected from the group consisting of hydrogen, a substituted or unsubstituted $C_6$-$C_{60}$ aryl, $C_6$-$C_{60}$ aryl, $C_6$-$C_{30}$ aryl, $C_6$-$C_{20}$ aryl, or $C_{12}$-$C_{20}$ aryl; and a substituted or unsubstituted $C_1$-$C_{60}$ heteroaryl, $C_1$-$C_{30}$ heteroaryl, $C_2$-$C_{20}$ heteroaryl, or $C_4$-$C_{12}$ heteroaryl. Preferably, $R_a$, $R_b$, $R_a'$ and $R_b'$ are each independently selected from hydrogen, F, methyl, phenyl, naphthyl, or biphenyl, hydrogen. Most preferably, all $R_c$, $R_d$, $R_c'$ and $R_d'$ are hydrogen.

In Formulae (1), (2c), (3a), (3b), (3c) and (3d), respectively, $R_c$, $R_d$, $R_c'$ and $R_d'$ are each independently selected from the group consisting of hydrogen, deuterium, a substituted or unsubstituted $C_1$-$C_{20}$ alkyl, $C_1$-$C_{15}$ alkyl, $C_1$-$C_{10}$ alkyl, or $C_1$-$C_5$ alkyl; a substituted or unsubstituted $C_1$-$C_{20}$ alkoxy, $C_1$-$C_{15}$ alkoxy, $C_1$-$C_{10}$ alkoxy, or $C_1$-$C_5$ alkoxy; a substituted or unsubstituted $C_6$-$C_{20}$ aryl, $C_6$-$C_{18}$ aryl, or $C_6$-$C_{12}$ aryl; a substituted or unsubstituted $C_1$-$C_{20}$ heteroaryl, $C_4$-$C_{15}$ heteroaryl, or $C_5$-$C_{10}$ heteroaryl; a substituted or unsubstituted $C_6$-$C_{20}$ aryloxy, $C_6$-$C_{18}$ aryloxy, or $C_6$-$C_{12}$ aryloxy, a halogen, and a cyano. Preferably, $R_c$, $R_d$, $R_c'$ and $R_d'$ are each independently selected from hydrogen, F, methyl, phenyl, naphthyl, or biphenyl. In some embodiments, at least two of $R_c$, $R_d$, $R_c'$ and $R_d'$ are hydrogen, and preferably $R_c$ and $R_c'$ are hydrogen. More preferably, all $R_c$, $R_d$, $R_c'$ and $R_d'$ are hydrogen. In some other embodiments, at least one of $R_c$, $R_d$, $R_c'$ and $R_d'$ is F.

In some embodiments, the organic compound of the present invention is selected from the following compounds (1) through (16):

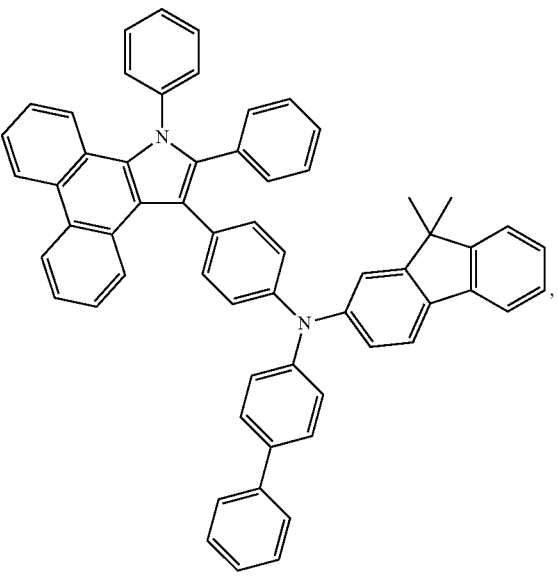
(1)

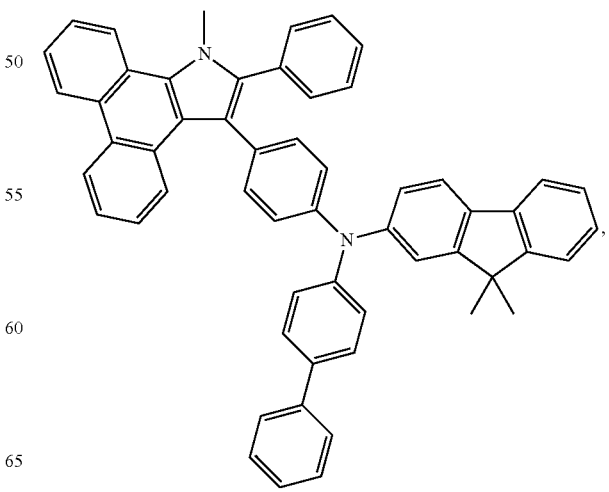
(2)

-continued
(3)
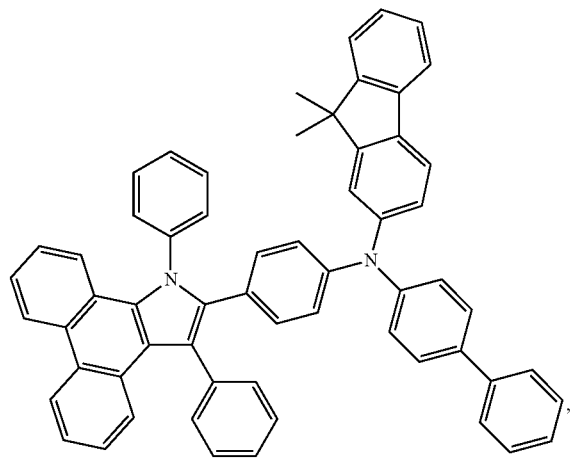
(4)
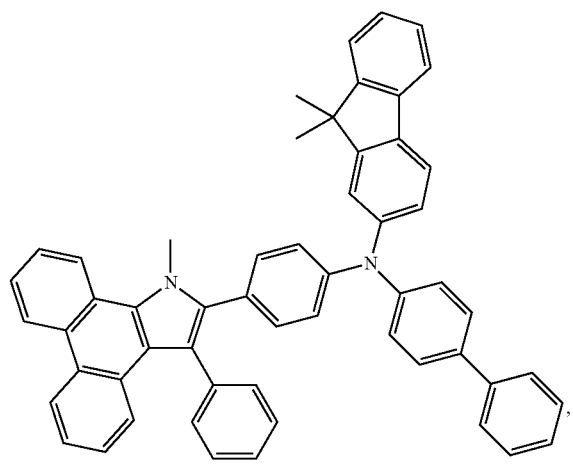
(5)
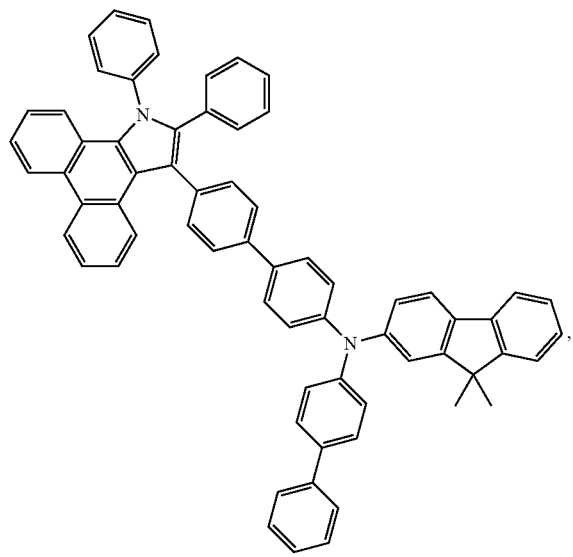
(6)
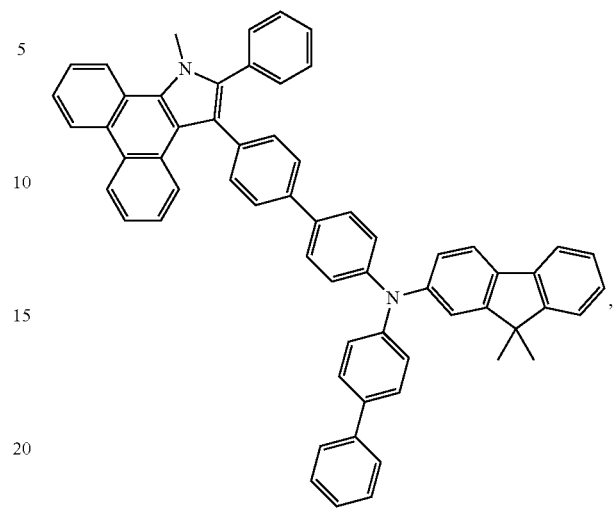
(7)
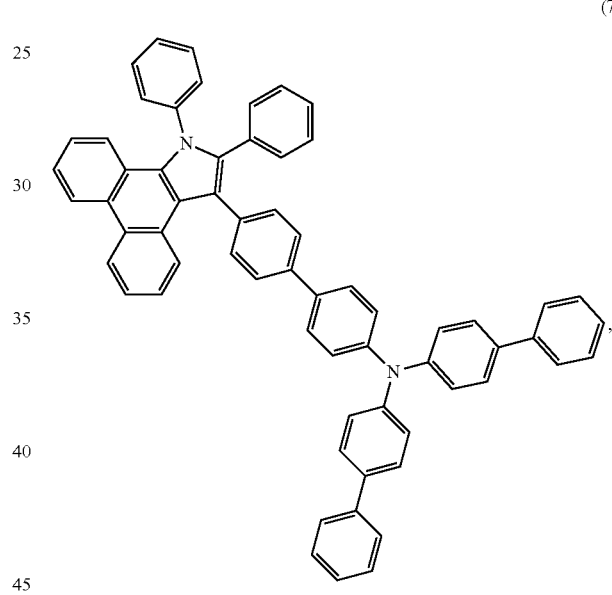
(8)
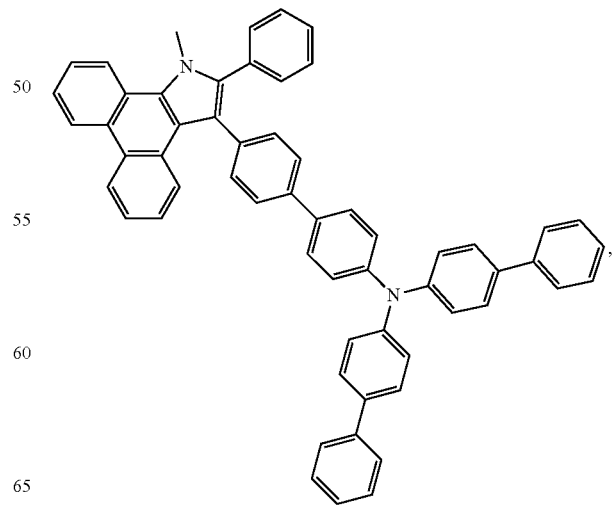

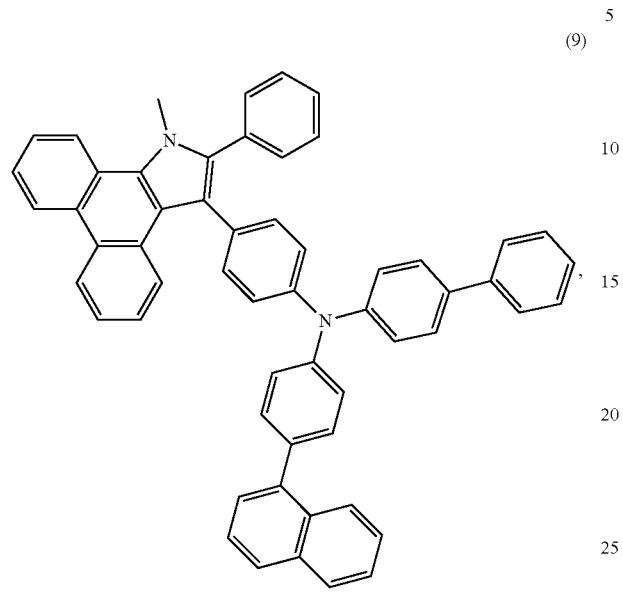
(9)
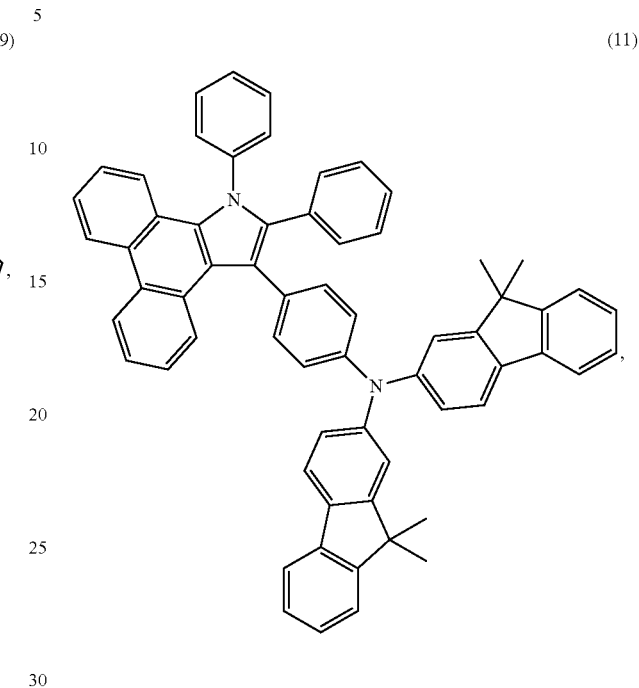
(11)
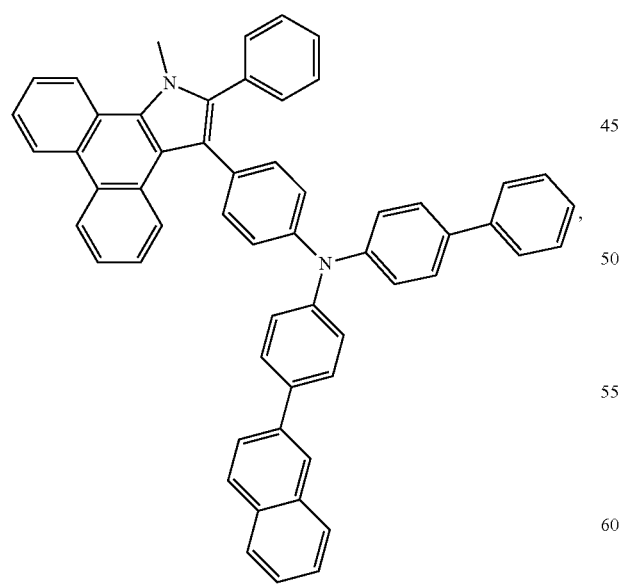
(10)
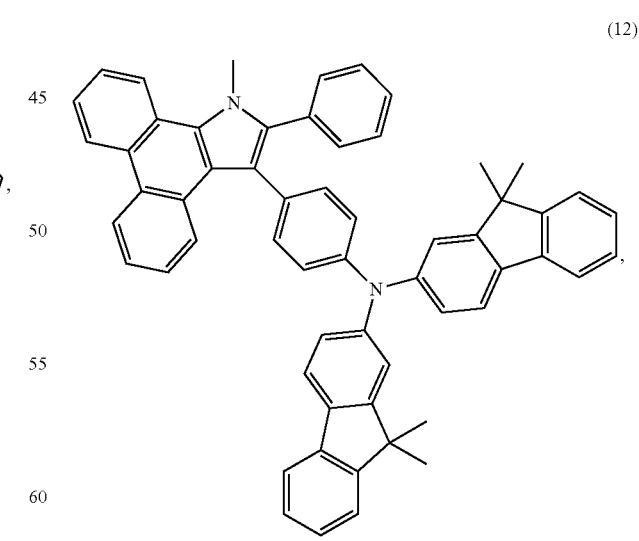
(12)

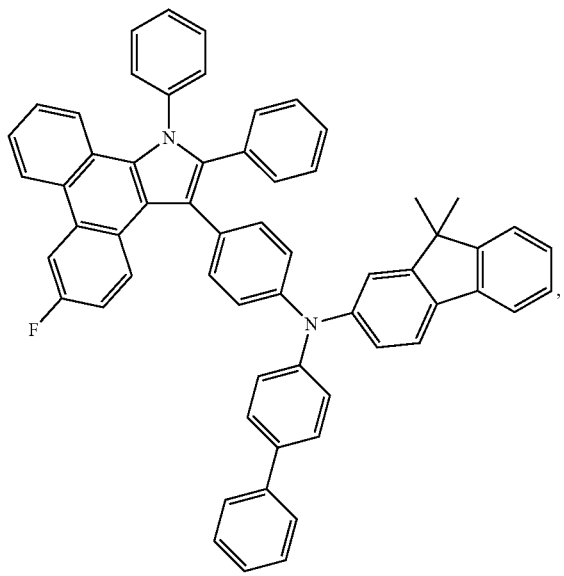

(13)

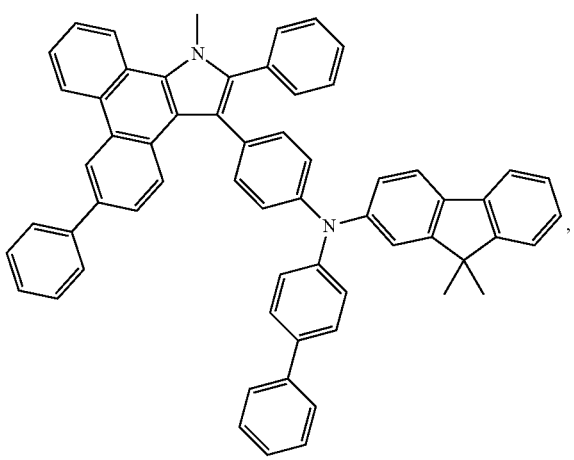

(14)

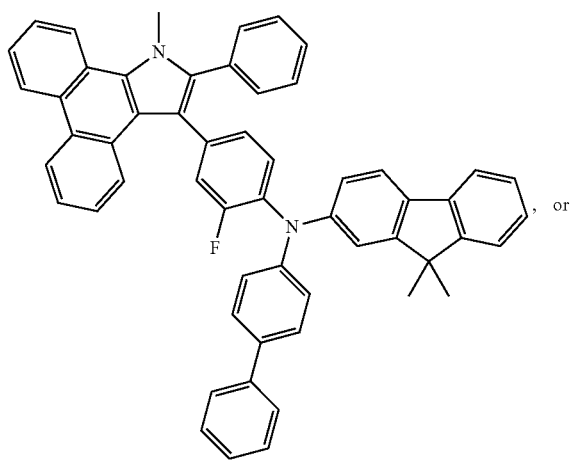

(15)

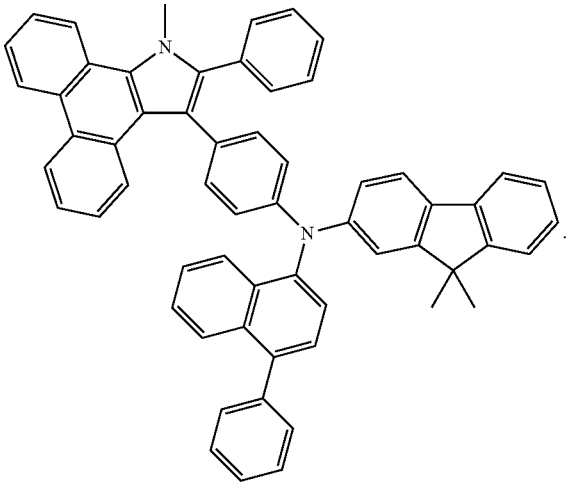

(16)

The organic compounds of the present invention may have a molecular weight up to 950 g/mole to be suitable for evaporative process. The organic compound may have a molecular weight of 500 g/mole or more, 600 g/mole or more, or even 700 g/mole or more, and at the same time, 950 g/mole or less, 900 g/mole or less, 850 g/mole or less, or even 800 g/mole or less.

The organic compounds of the present invention may have a high glass transition temperature ($T_g$). For example, $T_g$ of the organic compounds may be 110° C. or higher, 130° C. or higher, or 150° C. or higher, and at the same time, 250° C. or lower, 220° C. or lower, or even 200° C. or lower, as measured according to the test method described in the Examples section below.

The organic compounds of the present invention have good thermal stability. For example, the organic compounds may have a decomposition temperature ($T_d$) at 5% weight loss of 300° C. or higher, 350° C. or higher, or 400° C. or higher, and at the same time, 650° C. or lower, 600° C. or lower, or even 550° C. or lower, as measured according to the test method described in the Examples section below.

The organic compounds of the present invention may be prepared as shown in, for example, Scheme 1 below. 2-Bromobenzaldehyde derivative is first reacted with acetophenone via Aldol reaction to give a compound of Structure 1. The compound of Structure 1 is then reacted with benzaldehyde derivatives in THF via Stetter reaction to give a diketone intermediate, which is used to react with $R_5$—$NH_2$ to give a compound of Structure 2. An intramolecular cyclization is carried out to convert the compound of Structure 2 to a compound of Structure 3, followed by a bromination reaction to give a compound of Structure 4. The compound of Structure 4 undergoes a Suzuki coupling reaction to give the organic compound of Formula (3d), wherein $R_c$, $R_d$, $R_c'$, $R_d'$, $R_5$ $Ar_1$ and $Ar_2$ are as previously defined with reference to Formula (3d).

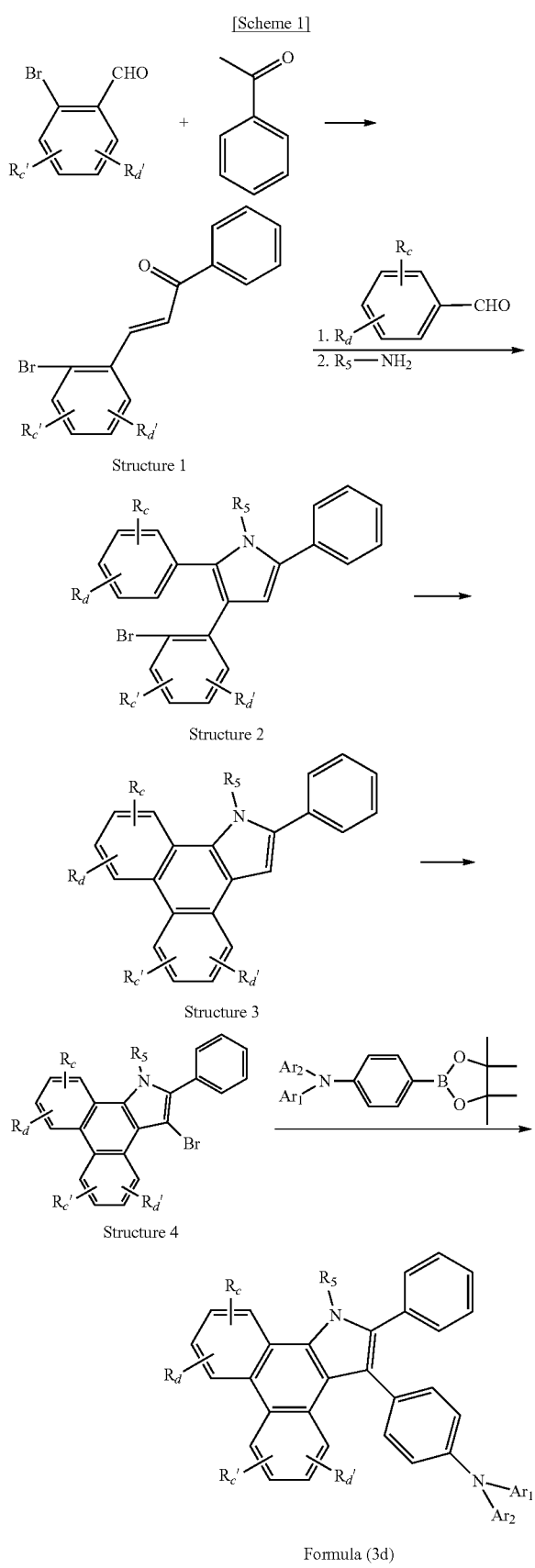

The organic compounds of the present invention may be used as charge transport layers and other organic layers in electronic devices, such as OLED devices. For example, the organic compound of the present invention may be used as charge blocking layers and charge generation layers.

The invention also provides a film comprising at least one layer comprising the organic compounds of the present invention described above.

The present invention also provides an electronic device comprising an organic layer comprising the organic compounds of the present invention. The electronic device may include organic photovoltaic, organic field effect transistor, and a light emitting device such as OLED devices. The term "light emitting device" herein refers to a device that emits light when an electrical current is applied across two electrodes.

The electronic device of the present invention may comprise a first electrode; a second electrode; and one or more organic layers interposed between the first electrode and the second electrode, wherein the organic layer comprises one or more organic compounds of the present invention. The organic layer can be a charge transfer layer that can transport charge carrying moieties, either holes or electrons. The organic layer may comprise a hole transport layer, an emissive layer, an electron transport layer, or a hole injection layer. Preferably, the organic layer is a hole transport layer or a hole injection layer. In addition to the organic compounds of the present invention, the organic layer may comprise one or more dopants. "Dopant" refers to an electron acceptor or a donator that increases the conductivity of an organic layer of an organic electronic device, when added to the organic layer as an additive. Organic electronic devices may likewise be influenced, with regard to their electrical conductivity, by doping. The organic layer comprising the organic compound of the present invention may be prepared by evaporative vacuum deposition or solution process such as spin coating and ink-jet printing.

In the present invention, "aryl" refers to an organic radical derived from aromatic hydrocarbon by the removal of one hydrogen atom therefrom. An aryl group may be a monocyclic and/or fused ring system each ring of which suitably contains from 4 to 6, preferably from 5 or 6 atoms. Structures wherein two or more aryl groups are combined through single bond(s) are also included. Examples of aryls include phenyl, naphthyl, biphenyl, anthryl, indenyl, fluorenyl, benzofluorenyl, phenanthryl, triphenylenyl, pyrenyl, perylenyl, chrysenyl, naphtacenyl, fluoranthenyl and the like. The naphthyl may be 1-naphthyl or 2-naphthyl. The anthryl may be 1-anthryl, 2-anthryl or 9-anthryl. The fluorenyl may be any one of 1-fluorenyl, 2-fluorenyl, 3-fluorenyl, 4-fluorenyl and 9-fluorenyl.

In the present invention, "substituted aryl" refers to an aryl in which at least one hydrogen atom is substituted with a heteroatom or a chemical group containing at least one heteroatom. Heteroatoms may include, for example, O, N, P and S. The chemical group containing at least one heteroatom herein may include, for example, OR', NR'$_2$, PR'$_2$, P(=O)R'$_2$, SiR'$_3$; where each R' is hydrogen or a $C_1$-$C_{30}$ hydrocarbyl.

In the present invention, "heteroaryl" refers to an aryl group, in which at least one carbon atom or CH group or CH$_2$ group is substituted with a heteroatom (for example, B, N, O, S, P(=O), Si and P) or a chemical group containing at least one heteroatom. The heteroaryl may be a 5- or 6-membered monocyclic heteroaryl or a polycyclic heteroaryl which is fused with one or more benzene ring(s), and may be partially saturated. The structures having one or more heteroaryl group(s) bonded through a single bond are also included. The heteroaryl groups may include divalent aryl groups of which the heteroatoms are oxidized or quarternized to form N-oxides, quaternary salts, or the like. Specific examples include, for example, monocyclic heteroaryl groups, such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl; polycyclic heteroaryl groups, such as benzofuranyl, fluoreno[4, 3-b]benzofuranyl, benzothiophenyl, fluoreno[4,3-b]benzothiophenyl, isobenzofuranyl, benzimidazolyl, benzothiazolyl, benzisothiazolyl, benzisoxazolyl, benzoxazolyl, isoindolyl, indolyl, indazolyl, benzothia-diazolyl, quinolyl, isoquinolyl, cinnolinyl, quinazolinyl, quinoxalinyl, carbazolyl, phenanthridinyl and benzodioxolyl; and corresponding N-oxides (for example, pyridyl N-oxide, quinolyl N-oxide) and quaternary salts thereof.

In the present invention, "substituted heteroaryl" refers to a heteroaryl in which at least one hydrogen atom is substituted with a heteroatom or a chemical group containing at least one heteroatom. Heteroatoms may include, for example, O, N, P and S. The chemical group containing at least one heteroatom may include, for example, OR', NR'$_2$, PR'$_2$, P(=O)R'$_2$, or SiR'$_3$, wherein each R' is hydrogen or a $C_1$-$C_{30}$ hydrocarbyl.

In the present invention, "hydrocarbyl" refers to a chemical group containing only hydrogen and carbon atoms.

In the present invention, "alkyl" and other substituents containing "alkyl" moiety include both linear and branched species. Examples of alkyls include methyl, ethyl, propyl, iso-propyl, butyl, iso-butyl, tert-butyl, pentyl, or hexyl.

In the present invention, "substituted alkyl" refers to an alkyl in which at least one hydrogen atom is substituted with a heteroatom or a chemical group containing at least one heteroatom. Heteroatoms may include, for example, O, N, P and S. The chemical group containing at least one heteroatom herein may include, for example, OR', NR'$_2$, PR'$_2$, P(=O)R'$_2$, or SiR'$_3$; where each R' is hydrogen or a $C_1$-$C_{30}$ hydrocarbyl.

In the present invention, "cycloalkyl" includes a monocyclic hydrocarbon and a polycyclic hydrocarbon such as substituted or unsubstituted adamantyl or substituted or unsubstituted $C_7$-$C_{30}$ bicycloalkyl.

In the present invention, other substituted groups described herein have one or more substituents. Substituents may include, for example, deuterium, halogen, $C_1$-$C_{30}$ alkyl with or without halogen substituent(s), $C_6$-$C_{30}$ aryl, $C_1$-$C_{30}$ heteroaryl with or without $C_6$-$C_{30}$ aryl substituent(s), a 5- to 7-membered heterocycloalkyl containing one or more heteroatom(s) selected from, for example, B, N, O, S, P(=O), Si and P, a 5 to 7-membered heterocycloalkyl fused with one or more aromatic ring(s), $C_3$-$C_{30}$ cycloalkyl, $C_5$-$C_{30}$ cycloalkyl fused with one or more aromatic ring(s), tri($C_1$-$C_{30}$) alkylsilyl, di($C_1$-$C_{30}$)alkyl($C_6$-$C_{30}$)arylsilyl, tri($C_6$-$C_{30}$)arylsilyl, adamantyl, $C_7$-$C_{30}$ bicycloalkyl, $C_2$-$C_{30}$ alkenyl, $C_2$-$C_{30}$ alkynyl, cyano, carbazolyl; $BR_8R_9$, $PR_{10}R_{11}$, $P(=O)R_{12}R_{13}$ wherein $R_8$ through $R_{13}$ independently represent $C_1$-$C_{30}$ alkyl, $C_6$-$C_{30}$ aryl or $C_1$-$C_{30}$ heteroaryl; $C_1$-$C_{30}$ alkyloxy, $C_1$-$C_{30}$ alkylthio, $C_6$-$C_{30}$ aryloxy, $C_6$-$C_{30}$ arylthio, $C_1$-$C_{30}$ alkoxycarbonyl, $C_1$-$C_{30}$ alkylcarbonyl, $C_6$-$C_{30}$ arylcarbonyl, $C_6$-$C_{30}$ aryloxycarbonyl, $C_1$-$C_{30}$ alkoxycarbonyloxy, $C_1$-$C_{30}$ alkylcarbonyloxy, $C_6$-$C_{30}$ arylcarbonyloxy, $C_6$-$C_{30}$ aryloxycarbonyloxy, carboxyl, nitro and hydroxyl; or that the substituents are linked together to form a ring. For example, a substituent may form a ring structure with one or more atoms on the backbone molecule comprising said substituent.

In the present invention, "electronic device" refers to a device which depends on the principles of electronics and uses the manipulation of electron flow for its operation.

In the present invention, "light emitting device" refers to a device that emits light when an electrical current is applied across two electrodes.

EXAMPLES

The following examples illustrate embodiments of the present invention. All parts and percentages are by weight unless otherwise indicated.

All solvents and reagents were obtained from commercial vendors, and were used in the highest available purities, and/or when necessary, recrystallized before use. Dry solvents were obtained from an in-house purification/dispensing system (hexane, toluene, and tetrahydrofuran), or purchased from Sigma-Aldrich. All experiments involving "water sensitive compounds" were conducted in "oven dried" glassware, under nitrogen ($N_2$) atmosphere, or in a glovebox. Reactions were monitored by analytical thin-layer chromatography (TLC) on precoated aluminum plates (VWR 60 F254), visualized by UV light and/or potassium permanganate staining. Flash chromatography was performed on an ISCO COMBIFLASH system with GRACERESOLV cartridges.

| Material name | Chemical structure | Supplier* | CAS No. |
|---|---|---|---|
| 2-Bromobenzaldehyde | Br, CHO (benzene ring) | SCRC | 6630-33-7 |
| Acetophenone | (benzene ring with C(=O)CH$_3$) | SCRC | 98-86-2 |
| Methanamine (30% in alcohol) | $CH_3NH_2$ | SCRC | 74-89-5 |

-continued

| Material name | Chemical structure | Supplier* | CAS No. |
|---|---|---|---|
| Aniline | NH$_2$ (phenyl) | SCRC | 62-53-3 |
| 3-Ethyl-5-(2-hydroxyethyl)-4-methylthiazolium bromide | (structure) | SCRC | 54016-70-5 |
| N-bromosuccinimide | NBS | SCRC | 128-08-5 |
| 4-yl(9,9-diphenyl-9h-fluoren-2-yl)amine | (structure) | SCRC | 1268520-04-2 |
| 2-(Dicyclohexylphosphino)-2',4',6'-triisopropylbiphenyl | X-Phos | SCRC | 564483-18-7 |
| Tricyclohexylphosphonium tetrafluoroborate | (Pcy)$_3$HBF$_4$ | SCRC | 58656-04-5 |
| Palladium acetate | Pd(OAc)$_2$ | SCRC | 3375-31-3 |

*SCRC refers to Sinopharm Chemical Reagent Co., Ltd.

The following standard analytical equipment and methods are used in the Examples.

Modeling

All computations utilized the Gaussian09 program as described in Gaussian 09, Revision A.02, Frisch, M. J. et al., Gaussian, Inc., Wallingford Conn., 2009. The calculations were performed with the hybrid density functional theory (DFT) method, B3LYP as described in Becke, A. D. J. Chem. Phys. 1993, 98, 5648; Lee, C. et al., Phys. Rev B 1988, 37, 785; and Miehlich, B. et al. Chem. Phys. Lett. 1989, 157, 200; and the 6-31G* (5d) basis set as described in Ditchfield, R. et al., J. Chem. Phys. 1971, 54, 724; Hehre, W. J. et al., J. Chem. Phys. 1972, 56, 2257; and Gordon, M. S. Chem. Phys. Lett. 1980, 76, 163. The singlet state calculations use the closed shell approximation, and the triplet state calculations use the open shell approximation. All values are quoted in electronvolts (eV). The highest occupied molecular orbital (HOMO) and lowest unoccupied molecular orbital (LUMO) values are determined from the orbital energies of the optimized geometry of the singlet ground state. The triplet energies are determined as the difference between the total energy of the optimized triplet state and the optimized singlet state. A procedure, as described in Lin, B. C et al., J. Phys. Chem. A 2003, 107, 5241-5251, is applied to calculate the reorganization energy of each molecule, with which as the indicator of electron and hole mobility.

NMR $^1$H-NMR spectra (500 MHZ or 400 MHZ) are obtained on a Varian VNMRS-500 or VNMRS-400 spectrometer at 30° C. The chemical shifts are referenced to tetramethyl silane (TMS) (δ:000) in CDCl$_3$.

Differential Scanning Calorimetry (DSC)

DSC measurements are carried out on a TA Instruments Q2000 instrument at a scan rate of 10° C./min under N$_2$ atmosphere for all cycles. The sample (about 7-10 mg) is scanned from room temperature to 300° C., cooled to −60° C., and reheated to 300° C. T$_g$ is measured on the second heating scan. Data analysis is performed using TA Universal Analysis software. The T$_g$ value is calculated using an "onset-at-inflection" methodology.

Thermal Gravimetric Analysis (TGA)

TGA measurements are carried out on a TA Instruments TGA-Q500 under N$_2$ atmosphere. The sample (about 7-10 mg) is weighed in a platinum standard plate and loaded into the instrument. The sample is first heated to 60° C. and equilibrated for 30 minutes to remove solvent residues in the sample. Then the sample is cooled to 30° C. The temperature is ramped from 30° C. to 600° C. with 10° C./min rate and the weight change is recorded to determine the decomposition temperature (T$_d$) of the sample. The temperature-weight % (T-Wt %) curve is obtained by TGA scan. The temperature at the 5% weight loss is determined as T$_d$.

Liquid Chromatography—Mass Spectrometry (LC/MS)

A sample is dissolved in tetrahydrofuran (THF) at around 0.6 mg/mL. 5 μL sample solution is injected on an Agilent 1220 HPLC/G6224A TOF mass spectrometer. The following analysis conditions are used:

Column: 4.6×150 mm, 3.5 μm ZORBAX Eclipse Plus C18; column temperature: 40° C.; Mobile phase: THF/deioned (DI) water=65/35 volume ratio (Isocratic method); Flow rate: 1.0 mL/min; and MS conditions: Capillary Voltage: 3500 kV (Pos); Mode: Pos; Scan: 100-2000 amu; Rate: 1 s/scan; and Desolvation temperature: 300° C.

High Performance Liquid Chromatography (HPLC)

A sample is dissolved in THF at around 0.6 mg/mL. The sample solution is at last filtrated through a 0.45 μm syringe filter and 5 μL of the filtrate is injected to HPLC system. The following analysis conditions are used:

Injection volume: 5 μL; Instrument: Agilent 1200 HPLC; Column: 4.6×150 mm, 3.5 μm ZORBAX Eclipse Plus C18; Column temperature: 40° C.; Detector: DAD=250, 280, 350 nm; Mobile Phase: THF/DI water=65/35 volume ratio (Isocratic method); and Flow rate: 1 mL/min.

Example (Ex) 1 Synthesis of HTL-75

The synthetic route of HTL-75 is shown as follows,

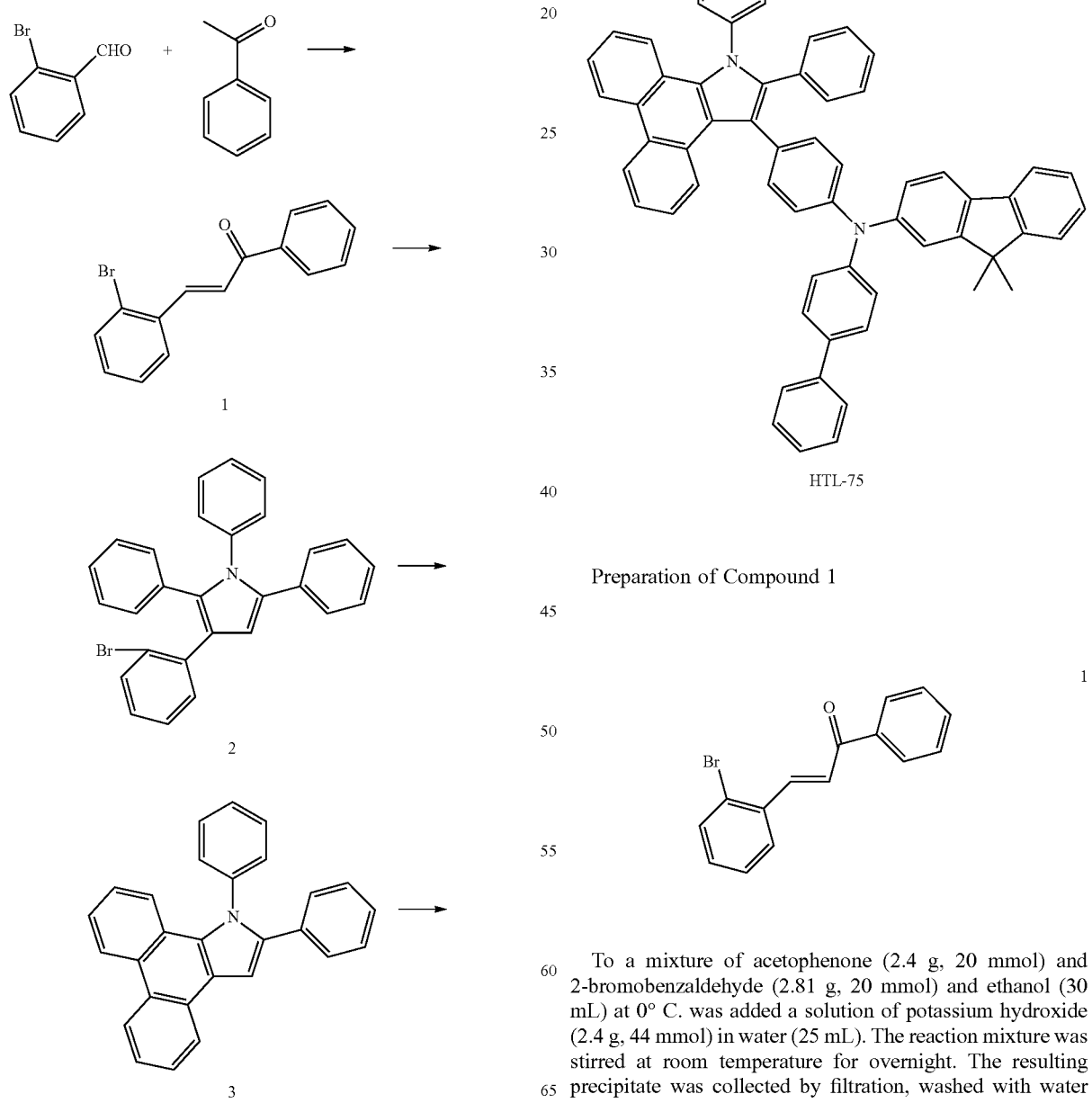

Preparation of Compound 1

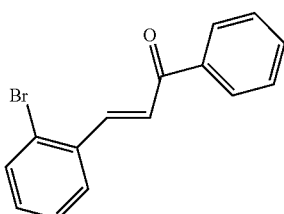

To a mixture of acetophenone (2.4 g, 20 mmol) and 2-bromobenzaldehyde (2.81 g, 20 mmol) and ethanol (30 mL) at 0° C. was added a solution of potassium hydroxide (2.4 g, 44 mmol) in water (25 mL). The reaction mixture was stirred at room temperature for overnight. The resulting precipitate was collected by filtration, washed with water and dried under reduced pressure to give desired product 4.1 g (85% yield).

Preparation of Compound 2

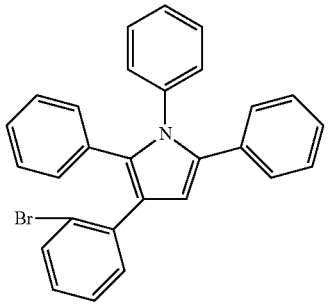

To a mixture of Compound 1 obtained above (2.87 g, 10.00 mmol, 287 g/mol), benzaldehyde (1.17 g, 11.00 mmol, 106 g/mol), 3-Ethyl-5-(2-hydroxyethyl)-4-methylthiazolium bromide (505 mg, 2.0 mmol) and $K_2CO_3$ (276 mg, 2.0 mmol) at room temperature was added THF (40 mL). The reaction mixture was stirred for 48 h at reflux. After completion of the reaction, the mixture was filtered to remove the salts and the solvents were removed by distillation under reduced pressure to afford crude products as yellow powders. The obtained powders, aniline (1.86 g, 20 mmol, 93 g/mol) in EtOH (60 mL) was added p-toluenesulfonic acid (TsOH) (20 mmol) and molecular sieves (10 g). The mixture was stirred at 80° C. overnight. After completion of the reaction, DI water was added to quench the reaction and filtered first and washed with dichloromethane (DCM). The solvents were removed and purified using column (eluent Petroleum ether (PE)/DCM=10:1) to give the products as white crystals (yield about 60% over 2 steps). $^1$H NMR (400 MHz, $CDCl_3$, ppm): 7.65-7.67 (d, J=8.0 Hz, 2H), 7.49-7.51 (m, 4H), 7.35-7.43 (m, 12H), 7.05-7.09 (m, 2H). LC-MS-ESI (m/z): calculated mass for $C_{28}H_{20}BrN$ 449.08, found $(M+H)^+$450.0848.

Preparation of Compound 3

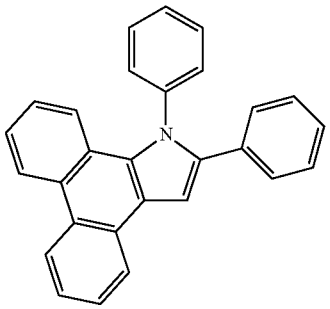

To a mixture of Compound 2 obtained above (4.5 g, 10.0 mmol, 450 g/mol), $K_2CO_3$ (20 mmol, 2.76 g, 138 g/mol) in Dimethylacetamide (DMA) (80 mL) was added $Pd(OAc)_2$ (2 mol %, 224 g/mmol, 45 mg), $PCy_3 \cdot HBF_4$ (4 mol %, 338 g/mol, 135 mg). The reaction mixture was stirred at 130° C. for about 12 hours. TLC was utilized to monitor the reaction. After completion of the reaction, DI water was added to quench the reaction and was extracted with dichloromethane. The combined extracts were washed with water, brine, dried over $Na_2SO_4$ and filtered. The solvents were removed and recrystallized in EtOH to give products as white powders (yield: about 90%). $^1$H NMR (400 MHz, $CDCl_3$, ppm): 8.31-8.33 (d, J=8.0 Hz, 1H), 8.25-8.27 (d, J=8.0 Hz, 1H), 8.07-8.09 (d, J=8.0 Hz, 1H), 7.49-7.52 (m, 1H), 7.38-7.46 (m, 6H), 7.16-7.29 (m, 6H), 7.10-7.13 (m, 2H), 7.05-7.10 (m, 1H). LC-MS-ESI (m/z): calculated mass for $C_{28}H_{19}N$ 369.15, found $(M+H)^+$370.1587.

Preparation of Compound 4

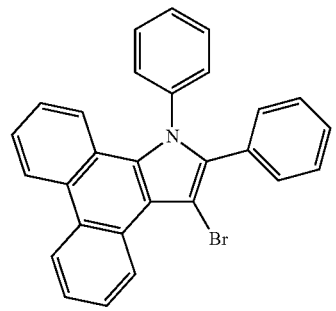

To a mixture of Compound 3 obtained above (3.69 g, 10.0 mmol, 369 g/mol) in DMA (50 mL) was added NBS (1.87 g, 10.5 mmol, 178 g/mol) at 0° C. The reaction mixture was stirred at r.t overnight. TLC was utilized to monitor the reaction. After completion of the reaction, DI water was added to quench the reaction and was extracted with EtOAc. The combined extracts were washed with water, brine and dried over $Na_2SO_4$, and filtered. The solvents were removed and recrystallized in EtOH to give the products as light yellow powders (yield above 90%). $^1$H NMR (400 MHz, $CDCl_3$, ppm): 9.52-9.54 (d, J=8.0 Hz, 1H), 8.72-8.74 (d, J=8.0 Hz, 2H), 7.68-7.72 (m, J=8.0 Hz, 1H), 7.59-7.63 (m, 1H), 7.39-7.47 (m, 4H), 7.27-7.30 (m, 7H), 7.10-7.19 (m, 2H). LC-MS-ESI (m/z): calculated mass for $C_{28}H_{18}BrN$ 447.06, found $(M+H)^+$448.0695.

Preparation of HTL-75

To a mixture of Compound 4 obtained above (4.48 g, 10 mmol, 448 g/mol), boric ester derivative (10 mmol, 5.64 g, 564 g/mol) in toluene (120 mL) was added $Pd(OAc)_2$ (2 mol %, 224 g/mmol, 45 mg), $PCy_3 \cdot HBF_4$ (4 mol %, 338 g/mol, 135 mg), $K_3PO_4$ (4.24 g, 20 mmol, 212 g/mol). The reaction mixture was stirred at reflux overnight under $N_2$ atmosphere. TLC was utilized to monitor the reaction. After completion of the reaction, DI water was added to quench the reaction and was extracted with EtOAc. The combined extracts were washed with water, brine, dried over $Na_2SO_4$, and filtered. The crude products were purified via silica gel column (eluent PE/DCM=10:1 to 5:1), and recrystalization in DCM/EtOH, DCM/PE and EtOAc subsequently to give products as white powders (crude yield about 90%, final yield about 70%, a purity of 99.7% as determined by HPLC. $^1$H NMR (400 MHz, $CDCl_3$, ppm): 8.09-8.11 (dd, J=8.0 Hz, 2H), 7.64-7.66 (d, J=8.0 Hz, 1H), 7.53-7.60 (m, 4H), 7.49-7.51 (m, 3H), 7.28-7.46 (m, 16H), 7.04-7.25 (m, 12H), 1.44 (s, 6H). LC-MS-ESI (m/z): calculated mass for $C_{61}H_{44}N_2$ 804.35, found $(M+H)^+$805.3615. The obtained HTL-75 has the structure as follows,

HTL-75

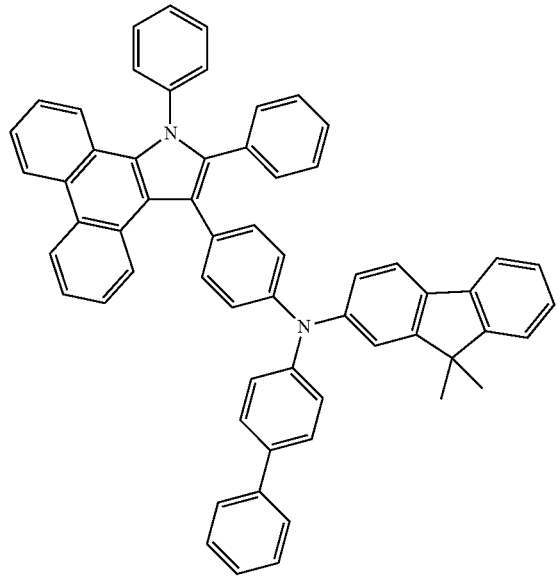

The obtained HTL-75 has a HOMO level of −4.73 eV, a LUMO level of −0.89 eV, a triplet energy of 2.62 eV, and a hole mobility level of 0.24, as determined by the modeling method described above.

Ex 2 Synthesis of HTL-77

The synthetic route of HTL-77 is shown as follows,

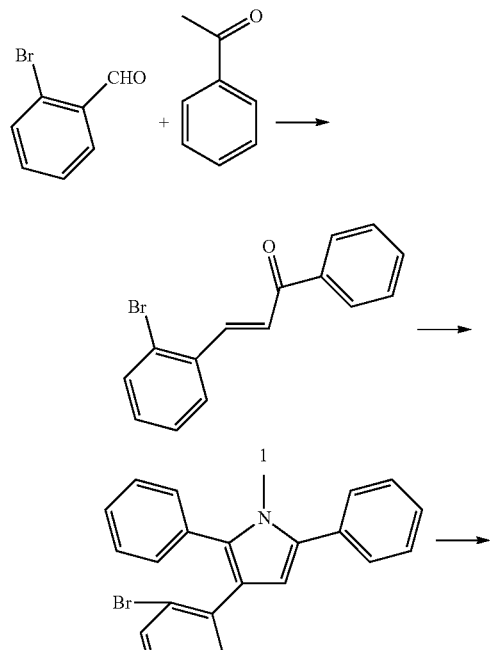

-continued

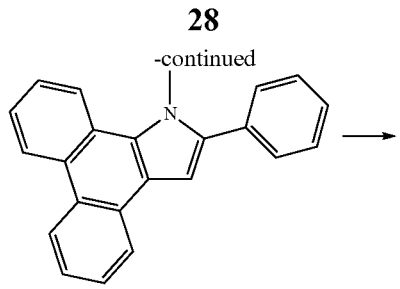

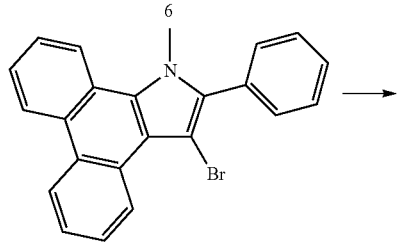

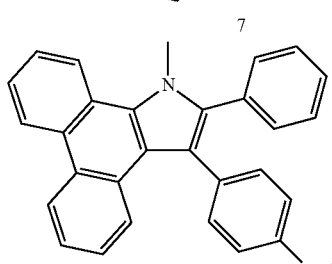

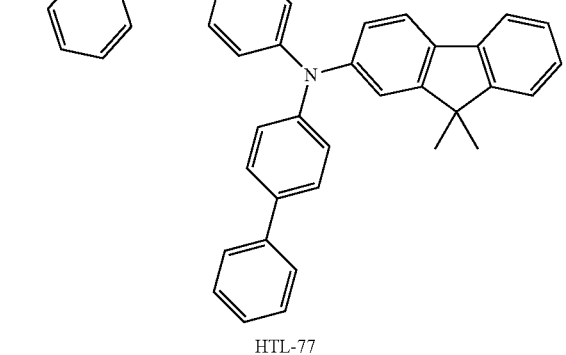

HTL-77

Preparation of Compound 5

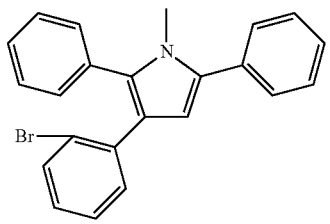

To a mixture of Compound 1 obtained above (2.87 g, 10.00 mmol, 287 g/mol), benzaldehyde (1.17 g, 11.00 mmol, 106 g/mol), 3-Ethyl-5-(2-hydroxyethyl)-4-methylthiazolium bromide (505 mg, 2.0 mmol) and $K_2CO_3$ (276 mg, 2.0 mmol) at r.t was added THF (40 mL). The reaction mixture was stirred for 48 h at reflux. After completion of the reaction, the mixture was filtered to remove the salts and the solvents were removed by distillation under reduced pressure to afford crude products as yellow powders. The obtained powders, methanamine (2.07 g, 20 mmol, 31 g/mol, 30% in alcohol) in EtOH (60 mL) was added TsOH (20 mmol) and molecular sieves (10 g). The mixture was stirred at 80° C. overnight. After completion of the reaction, DI water was added to quench the reaction and filtered first and washed with DCM. The solvents were removed and purified using column (eluent PE/DCM=10:1) to give the products as white crystals (yield about 60% over 2 steps). $^1$H NMR (400 MHz, CDCl$_3$, ppm): 7.54-7.57 (m, 3H), 7.42-7.46 (m, 2H), 7.22-7.34 (m, 6H), 7.07-7.09 (m, 2H), 6.99-7.09 (m, 1H), 6.49 (s, 1H), 3.58 (s, 3H). LC-MS-ESI (m/z): calculated mass for C$_{23}$H$_{18}$BrN 387.06, found (M+H)$^+$ 388.0695.

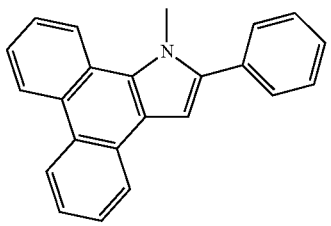

6

Preparation of Compound 6

To a mixture of the Compound 5 obtained above (3.88 g, 10.0 mmol, 388 g/mol), K$_2$CO$_3$ (20 mmol, 2.76 g, 138 g/mol) in DMA (80 mL) was added Pd(OAc)$_2$ (2 mol %, 224 g/mmol, 45 mg), PCy$_3$·HBF$_4$ (4 mol %, 338 g/mol, 135 mg). The reaction mixture was stirred at 130° C. overnight. TLC was utilized to monitor the reaction. After completion of the reaction, DI water was added to quench the reaction and was extracted with DCM. The combined extracts were washed with water, brine, dried over Na$_2$SO$_4$ and filtered. The solvents were removed and recrystallized in EtOH to give products as white powders (yield about 90%). $^1$H NMR (400 MHz, CDCl$_3$, ppm): 8.79-8.81 (d, J=8.0 Hz, 1H), 8.67-8.69 (d, J=8.0 Hz, 1H), 8.54-8.56 (d, J=8.0 Hz, 1H), 8.24-8.26 (d, J=8.0 Hz, 1H), 7.50-7.66 (m, 8H), 7.41-7.46 (m, 1H), 7.13 (s, 1H), 4.22 (s, 3H). LC-MS-ESI (m/z): calculated mass for C$_{23}$H$_{17}$N 307.14, found (M+H)$^+$308.1434.

Preparation of Compound 7

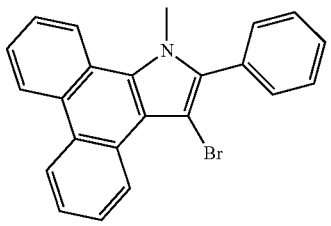

7

To a mixture of the Compound 6 obtained above (3.07 g, 10 mmol, 307 g/mol) in DMA (5 mL) was added NBS (1.87 g, 10.5 mmol, 178 g/mol) at 0° C. The reaction mixture was stirred at r.t overnight. TLC was utilized to monitor the reaction. After completion of the reaction, DI water was added to quench the reaction and was extracted with EtOAc. The combined extracts were washed with water, brine and dried over Na$_2$SO$_4$, and filtered. The solvents were removed and recrystallized in EtOH to give the products as light yellow powders (yield above 90%). $^1$H NMR (400 MHz, CDCl$_3$, ppm): 9.46-9.48 (d, J=8.0 Hz, 1H), 8.79-8.81 (d, J=8.0 Hz, 1H), 8.70-8.72 (d, J=8.0 Hz, 1H), 8.49-8.51 (d, J=8.0 Hz, 1H), 7.54-7.68 (m, 8H), 7.49-7.53 (m, 1H), 4.09 (s, 3H). LC-MS-ESI (m/z): calcd for C$_{23}$H$_{16}$BrN 385.05, found (M+H)$^+$386.0536.

Preparation of HTL-77

To a mixture of Compound 7 obtained above (3.86 g, 10 mmol, 386 g/mol), boric ester derivative (10 mmol, 5.64 g, 564 g/mol) in toluene (120 mL) was added Pd(OAc)$_2$ (2 mol %, 224 g/mmol, 45 mg), PCy$_3$·HBF$_4$ (4 mol %, 338 g/mol, 135 mg), K$_3$PO$_4$ (4.24 g, 20 mmol, 212 g/mol). The reaction mixture was stirred at reflux overnight under N$_2$ atmosphere. TLC was utilized to monitor the reaction. After completion of the reaction, DI water was added to quench the reaction and was extracted with EtOAc. The combined extracts were washed with water, brine, dried over Na$_2$SO$_4$, and filtered. The crude products were purified via silica gel column (eluent PE/DCM=10:1 to 5:1), and recrystalization in DCM/EtOH, DCM/PE and EtOAc subsequently to give products as white powders and a purity of 99.8% as determined by HPLC (crude yield about 90%, final yield about 70%). $^1$H NMR (400 MHz, CDCl$_3$, ppm): 8.81-8.83 (d, J=8.0 Hz, 1H), 8.69-8.71 (d, J=8.0 Hz, 1H), 8.59-8.61 (d, J=8.0 Hz, 1H), 8.02-8.04 (dd, J=8.0 Hz, 1H), 7.29-7.67 (m, 29H), 4.18 (s, 3H), 1.45 (s, 6H). LC-MS-ESI (m/z): calcd for C$_{56}$H$_{42}$N$_2$ 742.33, found (M+H)$^+$743.3403. The obtained HTL-77 has the structure as follows,

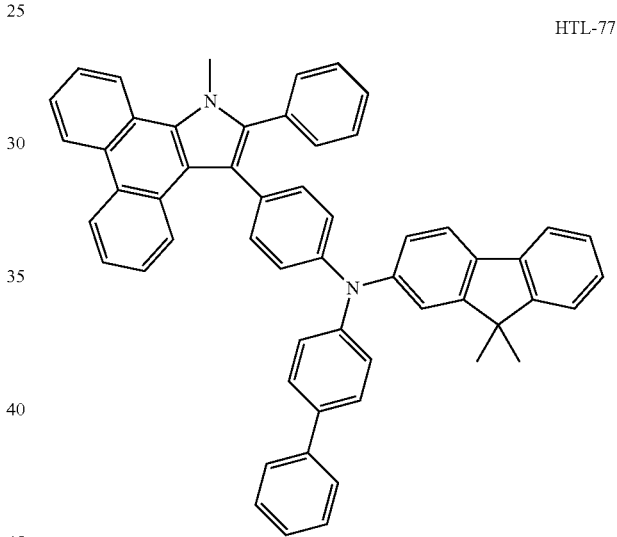

HTL-77

The obtained HTL-77 has a HOMO level of −4.74 eV, a LUMO level of −0.88 eV, a triplet energy of 2.62 eV, and a hole mobility level of 0.24, as determined by the modeling method described above.

Thermal properties of HTL-75 and HTL-77 were analyzed by DSC and TGA and results are shown in Table 1. As shown in Table 1, both HTL-75 and HTL-77 had a T$_g$ higher than 130.0° C. and a T$_d$ higher than 420° C.

TABLE 1

| Sample Name | T$_d$ [° C.] | T$_g$ [° C.] | T$_m$ [° C.] |
| --- | --- | --- | --- |
| HTL-75 | 428.3 | 145.2 | ND* |
| HTL-77 | 433.2 | 137.7 | ND* |

*No obvious T$_m$ was observed

Exs 3-4 OLED Device Fabrication

All organic materials were purified by sublimation before deposition. OLEDs were fabricated onto an ITO (Indium Tin Oxide) coated glass substrate that served as the anode, and topped with an aluminum cathode. All organic layers were thermally deposited by chemical vapor deposition, in a vacuum chamber with a base pressure of <$10^{-7}$ torr. The deposition rates of organic layers were maintained at 0.1~0.05 nm/s. The aluminum cathode was deposited at 0.5 nm/s. The active area of the OLED device was "3 mm×3 mm," as defined by the shadow mask for cathode deposition.

Each cell containing HIL (hole injection layer), HTL, EML (emitting material layer), ETL and EIL (electron injection layer), based on materials listed in Table 2, was placed inside a vacuum chamber, until it reached $10^{-6}$ torr. To evaporate each material, a controlled current was applied to the cell, containing the material, to raise the temperature of the cell. An adequate temperature was applied to keep the evaporation rate of the materials constant throughout the evaporation process.

For the hole injection layer, N4,N4'-diphenyl-N4,N4'-bis (9-phenyl-9H-carbazol-3-yl)-[1,1'-biphenyl]-4,4'-diamine was evaporated at a constant 1 A/s rate, until the thickness of the layer reached 600 Angstrom.

Simultaneously, the HTL compounds were evaporated at a constant 1 A/s rate, until the thickness reached 250 Angstrom.

For the emitting material layer, 9-phenyl-10-(4-phenyl-naphthalen-1-yl)anthracene (host) and N1,N6-bis(5'-fluoro-[1,1':3',1''-terphenyl]-4'-yl)-N1,N6-diphenylpyrene-1,6-diamine (dopant) were co-evaporated, until the thickness reached 200 Angstrom.

The deposition rate for host material was 1.0 A/s, and the deposition for the dopant material was 0.02 A/s, resulting in a 2% (by weight) doping of the host material. For ETL, 2,4-bis(9,9-dimethyl-9H-fluoren-2-yl)-6-(naphthalen-2-yl)-1,3,5-triazine was co-evaporated with lithium quinolate (Liq), until the thickness reached 300 Angstrom. The evaporation rate for the ETL compounds and Liq was 0.5 A/s. Finally, "20 Angstrom" of a thin electron injection layer (Liq) was evaporated at a 0.5 A/s rate.

The current-voltage-brightness (J-V-L) characterizations for the OLED devices were performed with a source measurement unit (KEITHLY 238) and a luminescence meter (MINOLTA CS-100A). Electroluminescence spectra of the OLED devices were collected by a calibrated CCD spectrograph. The results are shown in Table 3 below.

TABLE 2

| Name | | CAS No. |
|---|---|---|
| HIL compound | N4,N4'-diphenyl-N4,N4'-bis(9-phenyl-9H-carbazol-3-yl)-[1,1'-biphenyl]-4,4'-diamine | 887402-92-8 |
| HTL compound | Ex 3: HTL-75 Ex 4: HTL-77 | |
| Fl Blue Host | 9-phenyl-10-(4-phenylnaphthalen-1-yl)anthracene | 1207336-74-0 |
| Fl Blue Dopant | N1,N6-bis(5'-fluoro-[1,1':3',1''-terphenyl]-4'-yl)-N1,N6-diphenylpyrene-1,6-diamine | 1228525-73-2 |
| ETL compound | 2,4-bis(9,9-dimethyl-9H-fluoren-2-yl)-6-(naphthalen-2-yl)-1,3,5-triazine | 1459162-51-6 |
| EIL compound | lithium quinolate | 850918-68-2 |

As shown in Table 3, the inventive OLED devices comprising a layer containing HTL-75 or HTL-77 as HTL showed low driving voltage and high luminous efficiency. Surprisingly, the device comprising a layer of HTL-77 (Ex 4) showed significant higher luminous efficiency than the device comprising a layer of HTL-75 (Ex 3).

TABLE 3

| Device | HTL | Voltage@1000 nit [V] | Luminous Efficiency@ 1000 nit [Cd/A (candela per ampere)] | CIE* (X, Y) |
|---|---|---|---|---|
| Ex 3 | HTL-75 | 5.0 | 4.3 | 0.140, 0.089 |
| Ex 4 | HTL-77 | 4.8 | 6.6 | 0.141, 0.094 |

*CIE refers to International Commission on Illumination.

What is claimed is:

1. An organic compound having the structure represented by Formula (1):

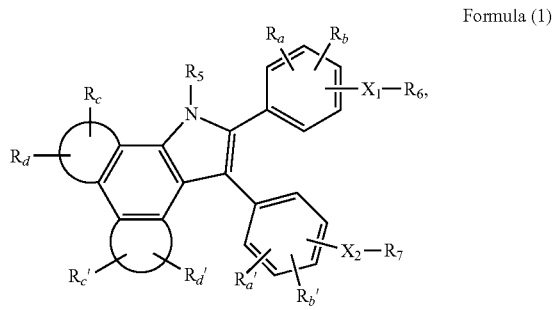

Formula (1)

wherein $R_c$, $R_d$, $R_c'$ and $R_d'$ are each independently selected from the group consisting of hydrogen, deuterium, a substituted or unsubstituted $C_1$-$C_{20}$ alkyl, a substituted or unsubstituted $C_1$-$C_{20}$ alkoxy, a substituted or unsubstituted $C_6$-$C_{20}$ aryl, a substituted or unsubstituted $C_1$-$C_{20}$ heteroaryl, a substituted or unsubstituted $C_6$-$C_{20}$ aryloxy, a halogen, and a cyano;

$R_5$ is selected from the group consisting of hydrogen, deuterium, a substituted or unsubstituted $C_1$-$C_{50}$ alkyl, a substituted or unsubstituted $C_3$-$C_{50}$ cycloalkyl, a substituted or unsubstituted $C_6$-$C_{60}$ aryl, and a substituted or unsubstituted $C_1$-$C_{60}$ heteroaryl;

$R_6$ and $R_7$ are each independently selected from the group consisting of hydrogen, deuterium, a substituted or unsubstituted $C_1$-$C_{50}$ alkyl, a substituted or unsubstituted $C_1$-$C_{50}$ alkoxy, a substituted or unsubstituted $C_1$-$C_{50}$ alkoxycarbonyl, a substituted or unsubstituted $C_6$-$C_{60}$ aryl, a substituted or unsubstituted $C_6$-$C_{60}$ aryloxy, a substituted or unsubstituted $C_6$-$C_{60}$ arylthio, a substituted or unsubstituted $C_1$-$C_{60}$ heteroaryl, a halogen, a cyano, a hydroxyl, a carbonyl, and an amino group substituted with a substituted or unsubstituted $C_6$-$C_{60}$ aryl or a substituted or unsubstituted $C_1$-$C_{60}$ heteroaryl; with the proviso that at least one of $R_6$ and $R_7$ is a substituted amino group having the structure of

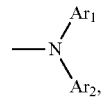

wherein $Ar_1$ and $Ar_2$ are each independently a substituted or unsubstituted $C_6$-$C_{60}$ aryl;

$R_a$, $R_b$, $R_a'$, and $R_b'$ are each independently selected from hydrogen, a substituted or unsubstituted $C_6$-$C_{60}$ aryl or a substituted or unsubstituted $C_1$-$C_{60}$ heteroaryl; and $X_1$ and $X_2$ are each a chemical bond, or each independently selected from the group consisting of a substituted or unsubstituted $C_1$-$C_{50}$ alkylene, a substituted or unsubstituted $C_3$-$C_{50}$ cycloalkylene, a substituted or unsubstituted $C_6$-$C_{60}$ arylene, and a substituted or unsubstituted $C_1$-$C_{60}$ heteroarylene; and optionally $X_1$ and $X_2$ may each independently form one or more rings with the rings they are bonded to.

2. The organic compound of claim 1, wherein the organic compound is represented by Formula (2a):

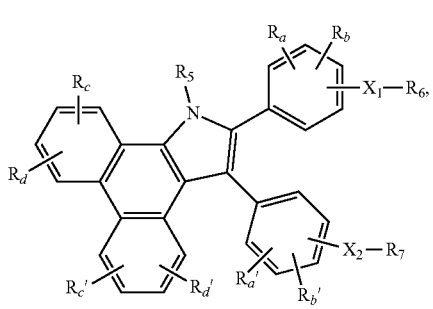

Formula (2a)

wherein $R_c$, $R_d$, $R_c'$ and $R_d'$ are each independently selected from the group consisting of hydrogen, deuterium, a substituted or unsubstituted $C_1$-$C_{20}$ alkyl, a substituted or unsubstituted $C_1$-$C_{20}$ alkoxy, a substituted or unsubstituted $C_6$-$C_{20}$ aryl, a substituted or unsubstituted $C_1$-$C_{20}$ heteroaryl, a substituted or unsubstituted $C_6$-$C_{20}$ aryloxy, a halogen, and a cyano;

$R_5$ is selected from the group consisting of hydrogen, deuterium, a substituted or unsubstituted $C_1$-$C_{50}$ alkyl, a substituted or unsubstituted $C_3$-$C_{50}$ cycloalkyl, a substituted or unsubstituted $C_6$-$C_{60}$ aryl, and a substituted or unsubstituted $C_1$-$C_{60}$ heteroaryl;

$R_6$ and $R_7$ are each independently selected from the group consisting of hydrogen, deuterium, a substituted or unsubstituted $C_1$-$C_{50}$ alkyl, a substituted or unsubstituted $C_1$-$C_{50}$ alkoxy, a substituted or unsubstituted $C_1$-$C_{50}$ alkoxycarbonyl, a substituted or unsubstituted $C_6$-$C_{60}$ aryl, a substituted or unsubstituted $C_6$-$C_{60}$ aryloxy, a substituted or unsubstituted $C_6$-$C_{60}$ arylthio, a substituted or unsubstituted $C_1$-$C_{60}$ heteroaryl, a halogen, a cyano, a hydroxyl, a carbonyl, and an amino group substituted with a substituted or unsubstituted $C_6$-$C_{60}$ aryl or a substituted or unsubstituted $C_1$-$C_{60}$ heteroaryl; with the proviso that at least one of $R_6$ and $R_7$ is a substituted amino group having the structure of

wherein $Ar_1$ and $Ar_2$ are each independently a substituted or unsubstituted $C_6$-$C_{60}$ aryl;

$R_a$, $R_b$, $R_a'$, and $R_b'$ are each independently selected from hydrogen, a substituted or unsubstituted $C_6$-$C_{60}$ aryl or a substituted or unsubstituted $C_1$-$C_{60}$ heteroaryl; and $X_1$ and $X_2$ are each a chemical bond, or each independently selected from the group consisting of a substituted or unsubstituted $C_1$-$C_{50}$ alkylene, a substituted or unsubstituted $C_3$-$C_{50}$ cycloalkylene, a substituted or unsubstituted $C_6$-$C_{60}$ arylene, and a substituted or unsubstituted $C_1$-$C_{60}$ heteroarylene; and optionally $X_1$ and $X_2$ may each independently form one or more rings with the rings they are bonded to.

3. The organic compound of claim 1, wherein the organic compound is represented by Formula (2b):

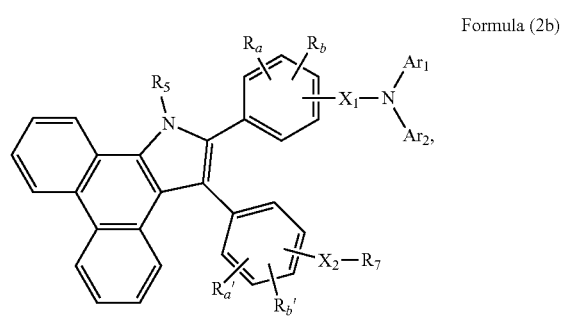

Formula (2b)

wherein $R_5$ is selected from the group consisting of hydrogen, deuterium, a substitute d or unsubstituted $C_1$-$C_{50}$ alkyl, a substituted or unsubstituted $C_3$-$C_{50}$ cycloalkyl, a substituted or unsubstituted $C_6$-$C_{60}$ aryl, and a substituted or unsubstituted $C_1$-$C_{60}$ heteroaryl;

$R_7$ is selected from the group consisting of hydrogen, deuterium, a substituted or unsubstituted $C_1$-$C_{50}$ alkyl, a substituted or unsubstituted $C_1$-$C_{50}$ alkoxy, a substituted or unsubstituted $C_1$-$C_{50}$ alkoxycarbonyl, a substituted or unsubstituted $C_6$-$C_{60}$ aryl, a substituted or unsubstituted $C_6$-$C_{60}$ aryloxy, a substituted or unsubstituted $C_6$-$C_{60}$ arylthio, a substituted or unsubstituted $C_1$-$C_{60}$ heteroaryl, a halogen, a cyano, a hydroxyl, and a carbonyl;

$R_a$, $R_b$, $R_a'$, and $R_b'$ are each independently selected from hydrogen, a substituted or unsubstituted $C_6$-$C_{60}$ aryl or a substituted or unsubstituted $C_1$-$C_{60}$ heteroaryl;

$Ar_1$ and $Ar_2$ are each independently a substituted or unsubstituted $C_6$-$C_{60}$ aryl; and $X_1$ and $X_2$ are each a chemical bond, or each independently selected from the group consisting of a substituted or unsubstituted $C_1$-$C_{50}$ alkylene, a substituted or unsubstituted $C_3$-$C_{50}$ cycloalkylene, a substituted or unsubstituted $C_6$-$C_{60}$ arylene, and a substituted or unsubstituted $C_1$-$C_{60}$ heteroarylene; and optionally $X_1$ and $X_2$ may each independently form one or more rings with the rings they are bonded to.

4. The organic compound of claim 1, wherein the organic compound is represented by Formula (2c):

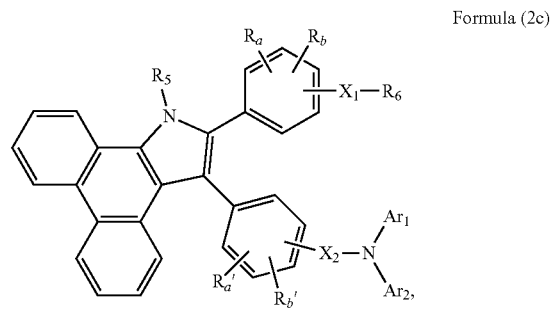

Formula (2c)

wherein $R_5$ is selected from the group consisting of hydrogen, deuterium, a substituted or unsubstituted $C_1$-$C_{50}$ alkyl, a substituted or unsubstituted $C_3$-$C_{50}$ cycloalkyl, a substituted or unsubstituted $C_6$-$C_{60}$ aryl, and a substituted or unsubstituted $C_1$-$C_{60}$ heteroaryl;

$R_6$ is selected from the group consisting of hydrogen, deuterium, a substituted or unsubstituted $C_1$-$C_{50}$ alkyl, a substituted or unsubstituted $C_1$-$C_{50}$ alkoxy, a substituted or unsubstituted $C_1$-$C_{50}$ alkoxycarbonyl, a substituted or unsubstituted $C_6$-$C_{60}$ aryl, a substituted or unsubstituted $C_6$-$C_{60}$ aryloxy, a substituted or unsubstituted $C_6$-$C_{60}$ arylthio, a substituted or unsubstituted $C_1$-$C_{60}$ heteroaryl, a halogen, a cyano, a hydroxyl, and a carbonyl;

$R_a$, $R_b$, $R_a'$, and $R_b'$ are each independently selected from hydrogen, a substituted or unsubstituted $C_6$-$C_{60}$ aryl or a substituted or unsubstituted $C_1$-$C_{60}$ heteroaryl;

$Ar_1$ and $Ar_2$ are each independently a substituted or unsubstituted $C_6$-$C_{60}$ aryl; and $X_1$ and $X_2$ are each a chemical bond, or each independently selected from the group consisting of a substituted or unsubstituted $C_1$-$C_{50}$ alkylene, a substituted or unsubstituted $C_3$-$C_{50}$ cycloalkylene, a substituted or unsubstituted $C_6$-$C_{60}$ arylene, and a substituted or unsubstituted $C_1$-$C_{60}$ heteroarylene; and optionally $X_1$ and $X_2$ may each independently form one or more rings with the rings they are bonded to.

5. The organic compound of claim 1, wherein the organic compound is represented by Formula (3a):

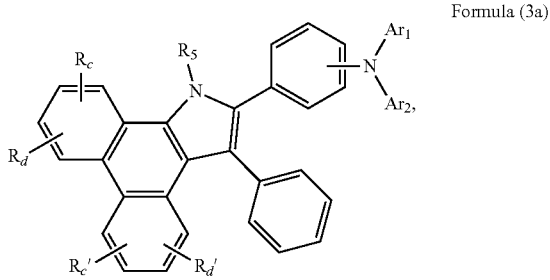

Formula (3a)

wherein $R_c$, $R_d$, $R_c'$ and $R_d'$ are each independently selected from the group consisting of hydrogen, deuterium, a substituted or unsubstituted $C_1$-$C_{20}$ alkyl, a substituted or unsubstituted $C_1$-$C_{20}$ alkoxy, a substituted or unsubstituted $C_6$-$C_{20}$ aryl, a substituted or unsubstituted $C_1$-$C_{20}$ heteroaryl, a substituted or unsubstituted $C_6$-$C_{20}$ aryloxy, a halogen, and a cyano;

$R_5$ is selected from the group consisting of hydrogen, deuterium, a substituted or unsubstituted $C_1$-$C_{50}$ alkyl, a substituted or unsubstituted $C_3$-$C_{50}$ cycloalkyl, a substituted or unsubstituted $C_6$-$C_{60}$ aryl, and a substituted or unsubstituted $C_1$-$C_{60}$ heteroaryl; and $Ar_1$ and $Ar_2$ are each independently a substituted or unsubstituted $C_6$-$C_{60}$ aryl.

6. The organic compound of claim 1, wherein the organic compound is represented by Formula (3b):

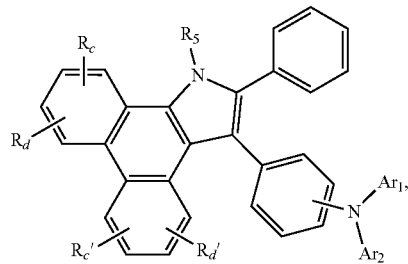

Formula (3b)

wherein $R_c$, $R_d$, $R_c'$ and $R_d'$ are each independently selected from the group consisting of hydrogen, deuterium, a substituted or unsubstituted $C_1$-$C_{20}$ alkyl, a substituted or unsubstituted $C_1$-$C_{20}$ alkoxy, a substituted or unsubstituted $C_6$-$C_{20}$ aryl, a substituted or unsubstituted $C_1$-$C_{20}$ heteroaryl, a substituted or unsubstituted $C_6$-$C_{20}$ aryloxy, a halogen, and a cyano;

$R_5$ is selected from the group consisting of hydrogen, deuterium, a substituted or unsubstituted $C_1$-$C_{50}$ alkyl, a substituted or unsubstituted $C_3$-$C_{50}$ cycloalkyl, a substituted or unsubstituted $C_6$-$C_{60}$ aryl, and a substituted or unsubstituted $C_1$-$C_{60}$ heteroaryl; and $Ar_1$ and $Ar_2$ are each independently a substituted or unsubstituted $C_6$-$C_{60}$ aryl.

7. The organic compound of claim 1, wherein $Ar_1$ and $Ar_2$ are each independently a substituted or unsubstituted $C_{12}$-$C_{20}$ aryl.

8. The organic compound of claim 1, wherein $R_c$, $R_d$, $R_c'$ and $R_d'$ are each hydrogen.

9. The organic compound of claim 1, wherein $R_a$, $R_b$, $R_a'$ and $R_b'$ are each independently selected from hydrogen or a substituted or unsubstituted $C_6$-$C_{20}$ aryl, and $X_1$ and $X_2$ are both chemical bonds.

10. The organic compound of claim 1, wherein at least one of $R_6$ and $R_7$ is selected from the following structures (5-1) through (5-6):

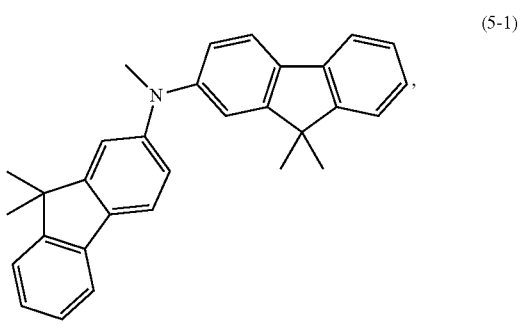

(5-1)

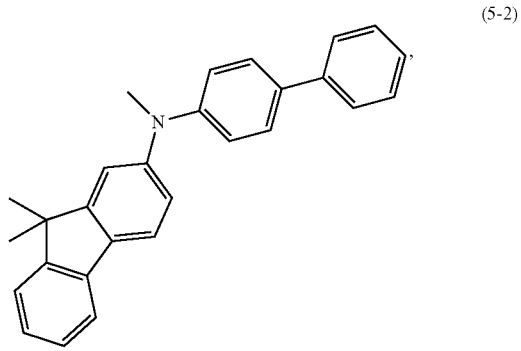

(5-2)

(5-3)
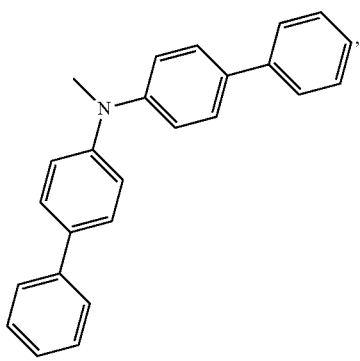
(5-4)
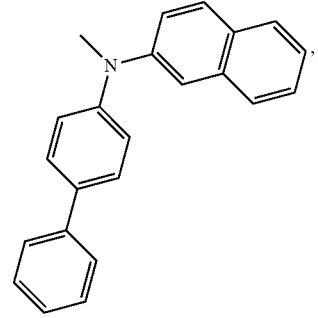
(5-5)
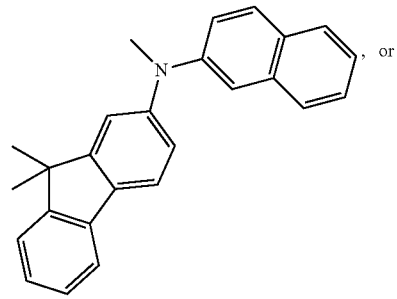, or
(5-6)
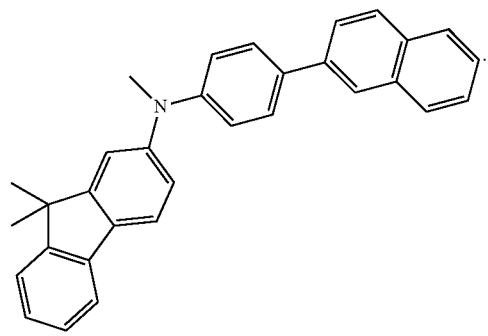
11. The organic compound of claim 1, wherein $R_5$ is selected from the group consisting of —$CH_3$, —$CH_2CH_3$, $CD_3$,
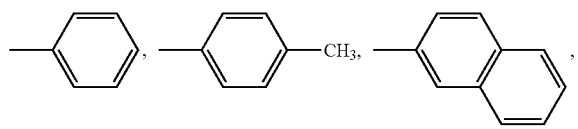
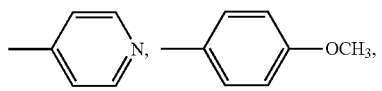
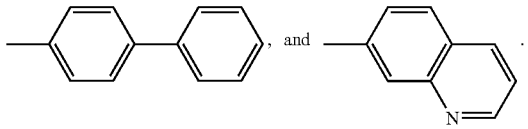
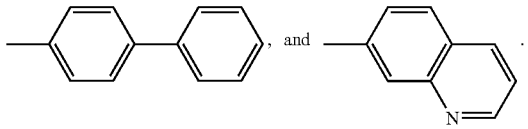
12. The organic compound of claim 1, wherein the organic compound is selected from the following compounds (1) through (20):
(1)
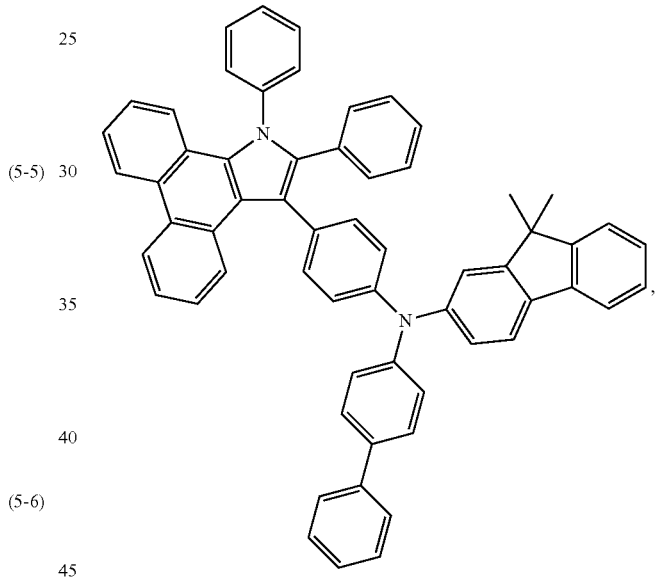
(2)
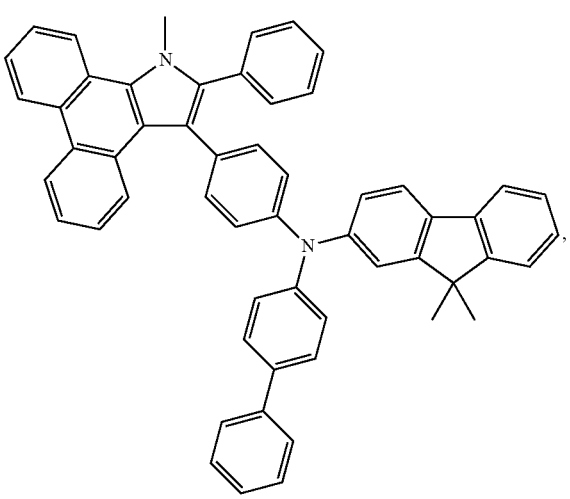

(3)
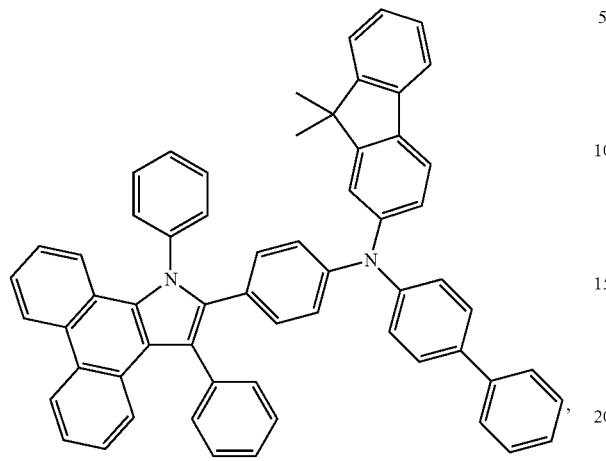
(4)
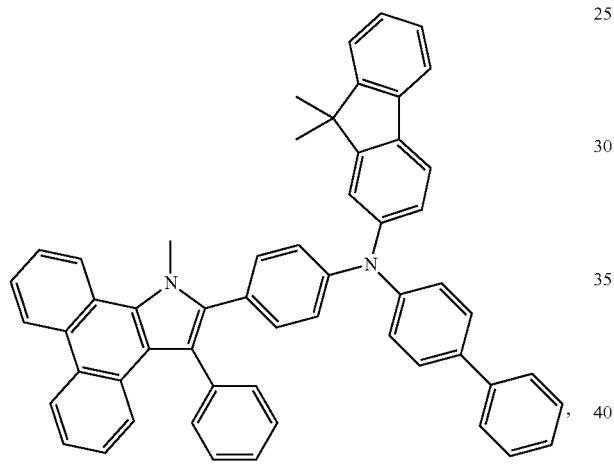
(5)
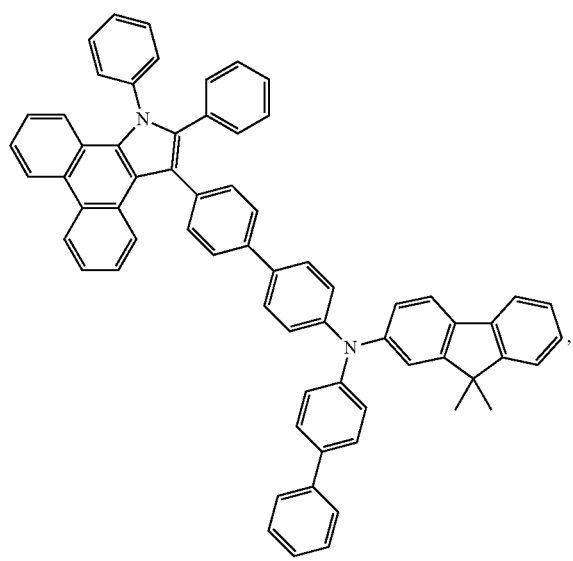
(6)
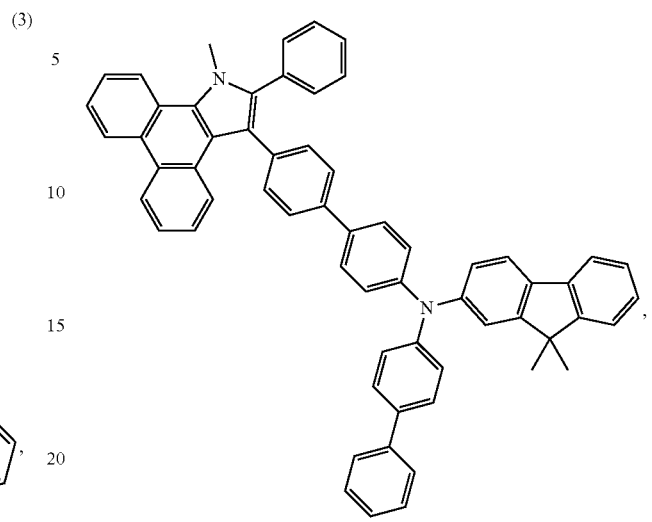
(7)
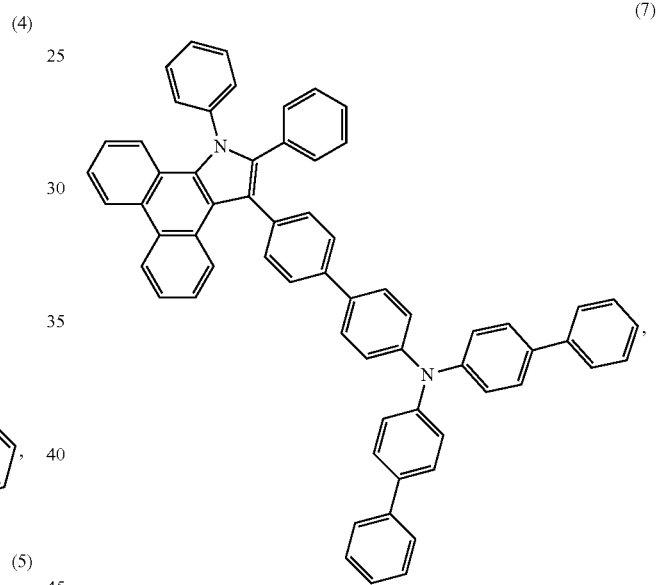
(8)
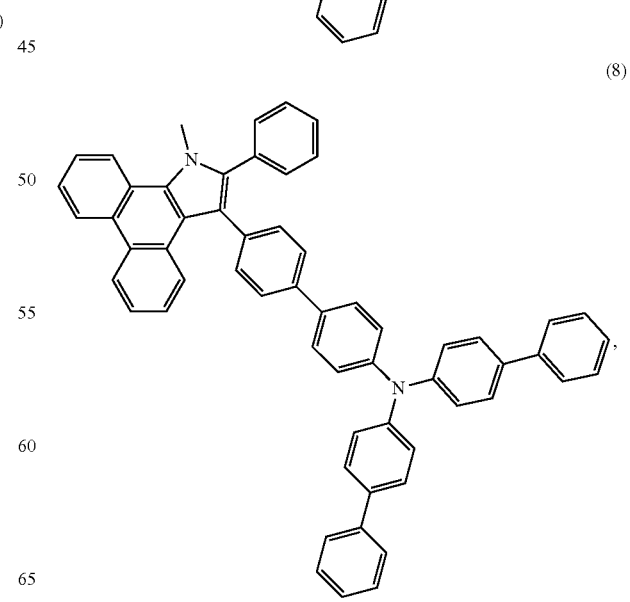

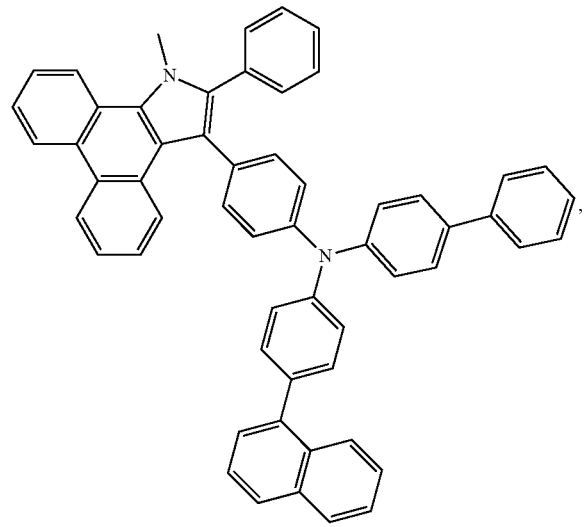
(9)
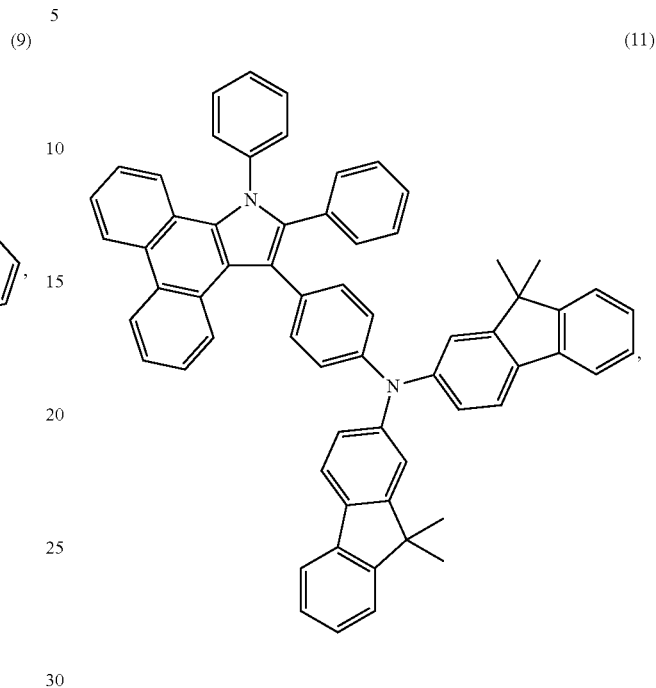
(11)
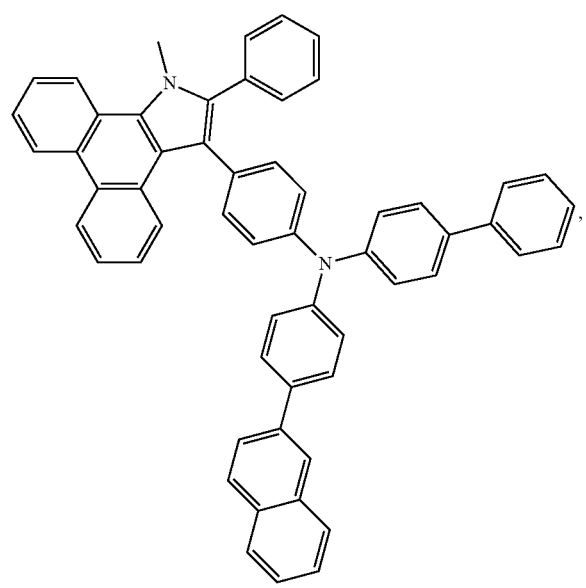
(10)
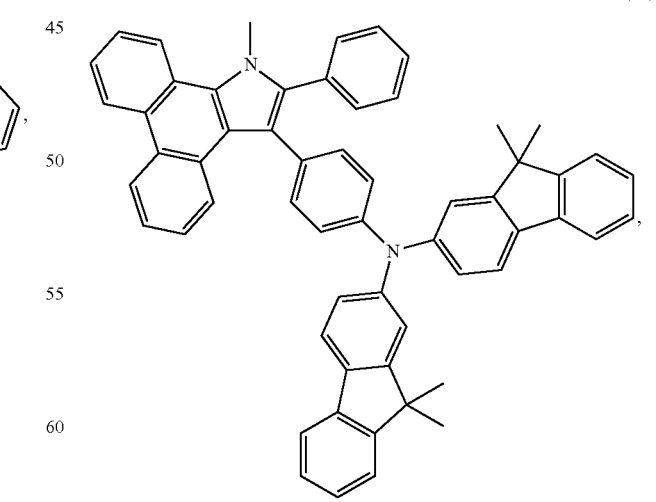
(12)

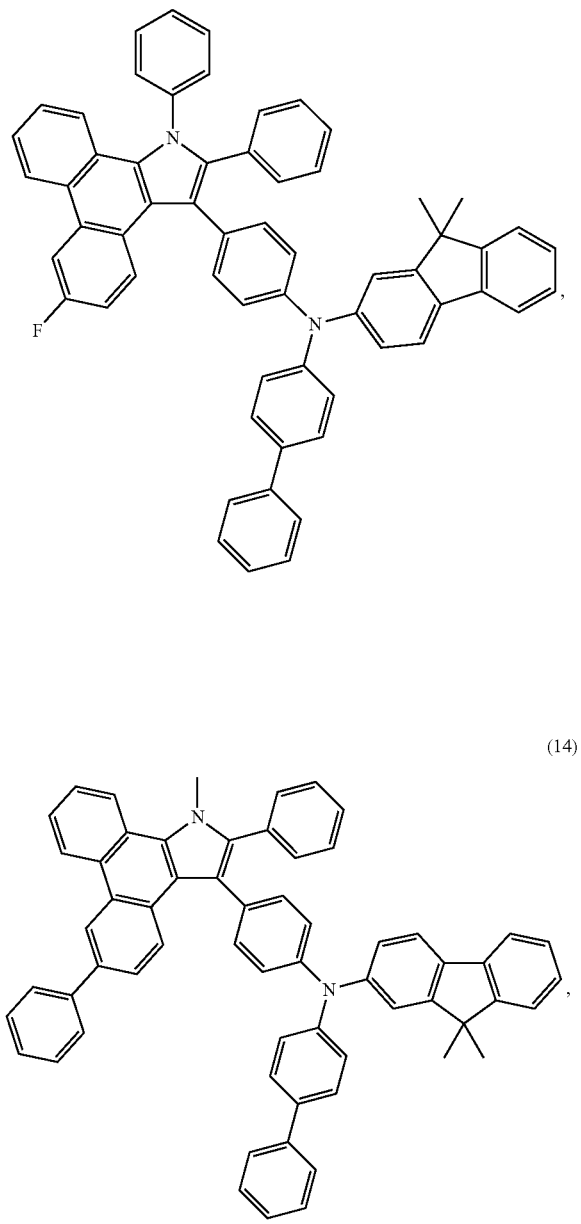

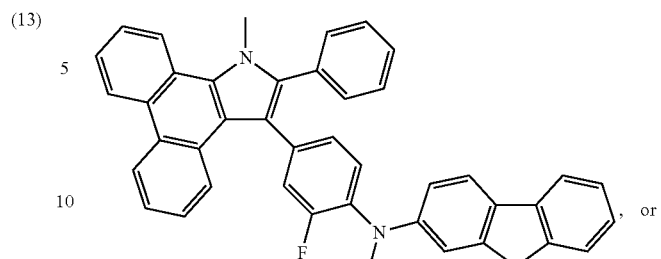

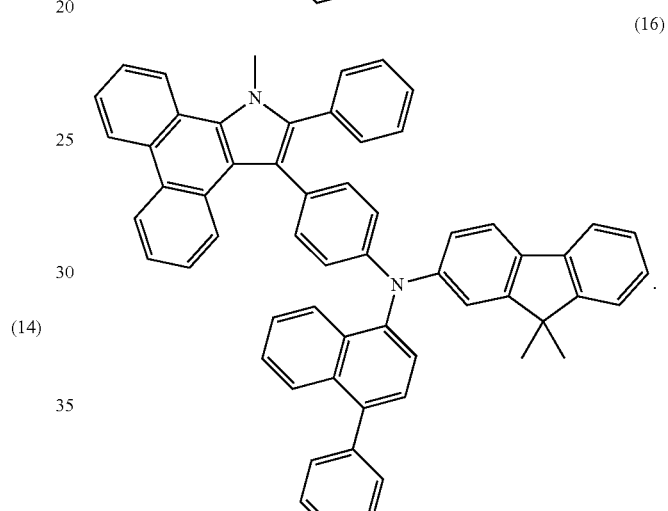

13. An electronic device comprising an organic layer, wherein the organic layer comprises the organic compound of claim 1.

14. The electronic device of claim 13, wherein the organic layer comprises a hole transport layer, an emissive layer, an electron transport layer, or a hole injection layer.

15. The electronic device of claim 13, wherein the electronic device is a light emitting device.

\* \* \* \* \*